(12) United States Patent
Blomquist et al.

(10) Patent No.: US 12,344,889 B2
(45) Date of Patent: *Jul. 1, 2025

(54) EXTRACTION-FREE PATHOGEN TESTING METHODS

(71) Applicants: Transformative Biotech, LLC, Boulder, CO (US); The Regents of The University of Colorado, Aurora, CO (US)

(72) Inventors: Robert E. Blomquist, Boulder, CO (US); Shi-Long Lu, Englewood, CO (US); Brian L. Harry, Denver, CO (US); Jose P. Zevallos, St. Louis, MO (US); Xin Yao, Boulder, CO (US)

(73) Assignees: Transformative Biotech, LLC, Boulder, CO (US); The Regents of the University of Colorado, Aurora, CO (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/690,951

(22) Filed: Mar. 9, 2022

(65) Prior Publication Data

US 2022/0290210 A1 Sep. 15, 2022

Related U.S. Application Data

(60) Provisional application No. 63/277,061, filed on Nov. 8, 2021, provisional application No. 63/158,685, filed on Mar. 9, 2021.

(51) Int. Cl.
*C12Q 1/68* (2018.01)
*C12Q 1/686* (2018.01)

(52) U.S. Cl.
CPC ......... *C12Q 1/686* (2013.01); *G01N 2800/26* (2013.01)

(58) Field of Classification Search
CPC .............................. C12Q 1/68; G01N 2800/26
See application file for complete search history.

(56) References Cited

U.S. PATENT DOCUMENTS

| | | | | |
|---|---|---|---|---|
| 6,777,210 B1 * | 8/2004 | Pasloske | .................. | C12N 9/22 536/25.1 |
| 7,319,021 B2 * | 1/2008 | Engel | .................. | C11D 3/3719 435/71.1 |
| 7,964,350 B1 * | 6/2011 | Fekete | ................. | C12Q 1/6844 536/25.4 |
| 2011/0081363 A1 * | 4/2011 | Whitney | .............. | C12Q 1/6806 435/235.1 |
| 2021/0341480 A1 * | 11/2021 | Lu | ......................... | C12Q 1/686 |
| 2022/0290210 A1 * | 9/2022 | Blomquist | ........... | C12Q 1/6806 |
| 2022/0356536 A1 * | 11/2022 | Beebe | ................. | B01L 3/50215 |
| 2023/0142838 A1 * | 5/2023 | Blomquist | ............. | C12Q 1/686 435/6.12 |

FOREIGN PATENT DOCUMENTS

| | | | | |
|---|---|---|---|---|
| EP | 3985129 A1 * | 4/2022 | .......... | C12Q 1/6876 |
| WO | WO-2013006793 A3 * | 5/2013 | .............. | C12Q 1/68 |
| WO | WO-2021133943 A1 * | 7/2021 | ............. | A61M 1/362 |
| WO | WO-2021168478 A1 * | 8/2021 | .......... | C12Q 1/6844 |
| WO | WO-2021202158 A1 * | 10/2021 | .......... | C12Q 1/6844 |
| WO | WO-2022020886 A1 * | 2/2022 | | |
| WO | WO-2022192440 A1 * | 9/2022 | .......... | C12Q 1/6806 |
| WO | WO-2022198086 A1 * | 9/2022 | | |
| WO | WO-2022236193 A2 * | 11/2022 | ............. | C12Q 1/701 |
| WO | WO-2023287901 A1 * | 1/2023 | .......... | C12Q 1/6806 |
| WO | WO-2023081029 A2 * | 5/2023 | .......... | C12Q 1/6806 |

OTHER PUBLICATIONS

Beltran-Pavez et al., 2020. SARS-COV-2 detection from nasopharyngeal swab samples without RNA extraction. Biorxiv, pp. 2020-03. (Year: 2020).*
Blow et al., 2004. Virus inactivation by nucleic acid extraction reagents. Journal of virological methods, 119(2), pp. 195-198. (Year: 2004).*
Fukumoto et al., 2020. Efficacy of a novel SARS-CoV-2 detection kit without RNA extraction and purification. International Journal of Infectious Diseases, 98, pp. 16-17. (Year: 2020).*
Hallick, 1977. Use of aurintricarboxylic acid as an inhibitor of nucleases during nucleic acid isolation. Nucleic acids research, 4(9), pp. 3055-3064. (Year: 1977).*
Jensen et al., Development of a novel real-time polymerase chain reaction assay for the quantitative detection of Nipah virus replicative viral RNA. PLoS One 2018, 13, e0199534, pp. 1-13. (Year: 2018).*
Liao et al., 2015. Enhancement of the antibiofilm activity of amphotericin B by polyamine biosynthesis inhibitors. International journal of antimicrobial agents, 46(1), pp. 45-52. (Year: 2015).*
Ngo et al., Unreliable Inactivation of Viruses by Commonly Used Lysis Buffers. Appl. Biosaf. 2017, 22, 56-59. (Year: 2017).*
Nie et al., 2012. Evaluation of a direct reverse transcription loop-mediated isothermal amplification method without RNA extraction for the detection of human enterovirus 71 subgenotype C4 in nasopharyngeal swab specimens. PloS one, 7(12) e52486, pp. 1-5. ( Year: 2012).*
Nishimura et al., 2000. Direct polymerase chain reaction from whole blood without DNA isolation. Annals of clinical biochemistry, 37 (5), pp. 674-680. (Year: 2000).*
Nishimura et al., 2010. Detection of noroviruses in fecal specimens by direct RT-PCR without RNA purification. Journal of virological methods, 163(2), pp. 282-286. (Year: 2010).*
Patterson et al., 2020. Methods of inactivation of SARS-CoV-2 for downstream biological assays. The Journal of infectious diseases, 222(9), pp. 1462-1467. (Year: 2020).*
Rabe et al., 2020. SARS-CoV-2 detection using isothermal amplification and a rapid, inexpensive protocol for sample inactivation and purification. Proceedings of the National Academy of Sciences, 117(39), pp. 24450-24458. (Year: 2020).*

(Continued)

*Primary Examiner* — Stephanie K Mummert
*Assistant Examiner* — Olayinka A Oyeyemi
(74) *Attorney, Agent, or Firm* — Thomas C. Meyers; Sullivan & Worcester LLP

(57) ABSTRACT

The invention provides compositions and methods allowing for rapid, accurate, robust, and low-cost diagnosis of infectious diseases via extraction-free, direct PCR techniques.

17 Claims, 32 Drawing Sheets

(56) References Cited

OTHER PUBLICATIONS

Smyrlaki et al., 2020. Massive and rapid COVID-19 testing is feasible by extraction-free SARS-CoV-2 RT-PCR. Nature communications, 11(1), 4812, p. 1-23. (Year: 2020).*
To et al., 2020. Temporal profiles of viral load in posterior oropharyngeal saliva samples and serum antibody responses during infection by SARS-CoV-2: an observational cohort study. The Lancet infectious diseases, 20(5), pp. 565-574. (Year: 2020).*
Wee et al., 2020. Rapid direct nucleic acid amplification test without RNA extraction for SARS-CoV-2 using a portable PCR thermocycler. Genes, 11(6), 664, pp. 1-13. (Year: 2020).*
Welch et al., 2020. Analysis of inactivation of SARS-CoV-2 by specimen transport media, nucleic acid extraction reagents, detergents, and fixatives. Journal of clinical microbiology, 58(11), e01713-20, pp. 1-13. (Year: 2020).*
Yang et al., 2007. A novel buffer system, AnyDirect, can improve polymerase chain reaction from whole blood without DNA isolation. Clinica chimica acta, 380(1-2), pp. 112-117. (Year: 2007).*
Mahalanabis, 2009. Cell lysis and DNA extraction of gram-positive and gram-negative bacteria from whole blood in a disposable microfluidic chip. Lab on a Chip, 9(19), pp. 2811-2817. (Year: 2009).*
Ben-Assa et al., 2020. SARS-CoV-2 on-the-spot virus detection directly from patients. MedRxiv, pp. 2020-04. (Year: 2020).*
Feng et al., 2020. Molecular diagnosis of COVID-19: challenges and research needs. Analytical chemistry, 92(15), pp. 10196-10209. (Year: 2020).*
Myhrvold et al., 2018. Field-deployable viral diagnostics using CRISPR-Cas13. Science, 360(6387), pp. 444-448. (Year: 2018).*
Walker, F.M. and Hsieh, K., 2019. Advances in directly amplifying nucleic acids from complex samples. Biosensors, 9(4), 117, pp. 1-29. (Year: 2019).*
Lalli et al., Aug. 6, 2020. Rapid and extraction-free detection of SARS-CoV-2 from saliva with colorimetric LAMP. MedRxiv, pp. 1-34. (Year: 2020).*
Lalli et al., 2021. Rapid and extraction-free detection of SARS-CoV-2 from saliva by colorimetric reverse-transcription loop-mediated isothermal amplification. Clinical chemistry, 67(2), pp. 415-424. (Year: 2021).*
Barza et al., Nov. 2020. Use of a simplified sample processing step without RNA extraction for direct SARS-CoV-2 RT-PCR detection. Journal of Clinical Virology, 132, 104587, pp. 1-3. (Year: 2020).*
Chu et al., Aug. 2020. Evaluation of simple nucleic acid extraction methods for the detection of SARS-CoV-2 in nasopharyngeal and saliva specimens during global shortage of extraction kits. Journal of Clinical Virology, 129, 104519, pp. 1-4. (Year: 2020).*
Genoud et al., Feb. 26, 2021. Extraction-free protocol combining proteinase K and heat inactivation for detection of SARS-CoV-2 by RT-qPCR. PLOS One, 16(2), e0247792, pp. 1-16. (Year: 2021).*
Lalli et al., Epub Oct. 24, 2020. Rapid and extraction-free detection of SARS-CoV-2 from saliva by colorimetric reverse-transcription loop-mediated isothermal amplification. 2021. Clinical chemistry, 67(2), pp. 415-424. (Year: 2020).*
Mallmann, May 9, 2020. Pre-treatment of the clinical sample with Proteinase K allows detection of SARS-CoV-2 in the absence of RNA extraction. Biorxiv, May 2020, pp. 1-6. (Year: 2020).*
Merindol et al. Jul. 2020. SARS-CoV-2 detection by direct rRT-PCR without RNA extraction. Journal of Clinical Virology, 128, 104423, pp. 1-4. (Year: 2020).*
Ponce-Rojas et al., Epub Jun. 30, 2020. A Fast and Accessible Method for the Isolation of RNA, DNA, and Protein to Facilitate the detection of SARS-CoV-2. UC Santa Barbara, pp. 1-9. (Year: 2020).*
Ponce-Rojas et al., Epub Mar. 19, 2021. A fast and accessible method for the isolation of RNA, DNA, and protein to facilitate the detection of SARS-CoV-2. Journal of clinical microbiology, Apr. 2021, 59(4), e02403-20, pp. 1-8. (Year: 2021).*
Rabe et al., Sep. 8, 2020. SARS-CoV-2 detection using isothermal amplification and a rapid, inexpensive protocol for sample inactivation and purification. PNAS, 117(39), pp. 24450-24458. (Year: 2020).*
Radbel et al., Jul. 2020. Detection of severe acute respiratory syndrome coronavirus 2 (SARS-CoV-2) is comparable in clinical samples preserved in saline or viral transport medium. The Journal of Molecular Diagnostics, 22(7), pp. 871-875. (Year: 2020).*
Rogers et al., Jul. 23, 2020. Evaluation of transport media and specimen transport conditions for the detection of SARS-CoV-2 by use of real-time reverse transcription-PCR. Journal of clinical microbiology, Aug. 2020, 58(8), e00708-20, pp. 1-5. (Year: 2020).*
Song et al., Sep. 20, 2021. Single-and two-stage, closed-tube, point-of-care, molecular detection of SARS-CoV-2. Analytical chemistry, 93(38), pp. 13063-13071. (Year: 2021).*
Tee et al., Mar. 5, 2021. Direct saliva versus conventional nasopharyngeal swab qRT-PCR to diagnose SARS-CoV2: Validity study. Asian J. Res. Infect. Dis, 6(2), pp. 37-46. (Year: 2021).*
Ulloa et al., Epub Aug. 22, 2020. A simple method for SARS-CoV-2 detection by rRT-PCR without the use of a commercial RNA extraction kit. Journal of virological methods, Nov. 2020, 285, 113960, pp. 1-3. (Year: 2020).*
Vindeirinho et al., Mar. 23, 2022. SARS-CoV-2 diagnostics based on nucleic acids amplification: from fundamental concepts to applications and beyond. Frontiers in cellular and infection microbiology, vol. 12, 799678, pp. 1-29. (Year: 2022).*
Vogels et al., Mar. 12, 2021. SalivaDirect: A simplified and flexible platform to enhance SARS-CoV-2 testing capacity. Med, 2(3), pp. 263-280. (Year: 2021).*
Wang et al., 2016. Endogenous RNase inhibitor contributes to stability of RNA in crude cell lysates: Applicability to RT-qPCR. Analytical biochemistry, 513, pp. 21-27. (Year: 2016).*
Wee et al., Jun. 18, 2020. Rapid direct nucleic acid amplification test without RNA extraction for SARS-CoV-2 using a portable PCR thermocycler. Genes, 11(6), 664, pp. 1-13. (Year: 2020).*
Zhang et al., Feb. 29, 2020. Rapid molecular detection of SARS-CoV-2 (COVID-19) virus RNA using colorimetric LAMP. MedRxiv, Feb. 2020, pp. 1-14. (Year: 2020).*
Li et al., 2011. A PCR amplification method without DNA extraction. Electrophoresis, 32(3-4), pp. 394-397. (Year: 2011).*
Anahtar et al., Epub Dec. 21, 2020. Clinical assessment and validation of a rapid and sensitive SARS-CoV-2 test using reverse transcription loop-mediated isothermal amplification without the need for RNA extraction. In Open Forum Infectious Diseases, 2021, Feb. 2021, 8(2), pp. 1-9. (Year: 2020).*
Ganguli et al., Aug. 31, 2020. Rapid isothermal amplification and portable detection system for SARS-CoV-2. PNAS, 117(37), pp. 22727-22735. (Year: 2020).*
Visseaux et al., Epub Feb. 9, 2021. Evaluation of three extraction-free SARS-CoV-2 RT-PCR assays: A feasible alternative approach with low technical requirements. Journal of Virological Methods, May 2021, 291, 114086, pp. 1-4. (Year: 2021).*
Wei et al., Jan. 28, 2021. Direct diagnostic testing of SARS-CoV-2 without the need for prior RNA extraction. Scientific reports, 11(1), 2402, pp. 1-6. (Year: 2021).*
Graham et al., Feb. 3, 2021. Open-source RNA extraction and RT-qPCR methods for SARS-CoV-2 detection. PloS one, 16(2), e0246647, pp. 1-24. (Year: 2021).*
Smith et al., Jul. 23, 2020. Large-scale, in-house production of viral transport media to support SARS-CoV-2 PCR testing in a multi-hospital health care network during the COVID-19 pandemic. Journal of Clinical Microbiology, 58(8), pp. 1-7. (Year: 2020).*
Dao et al., Aug. 12, 2020. A colorimetric RT-LAMP assay and LAMP-sequencing for detecting SARS-CoV-2 RNA in clinical samples. Science translational medicine, 12(556), eabc7075, pp. 1-13. (Year: 2020).*

\* cited by examiner

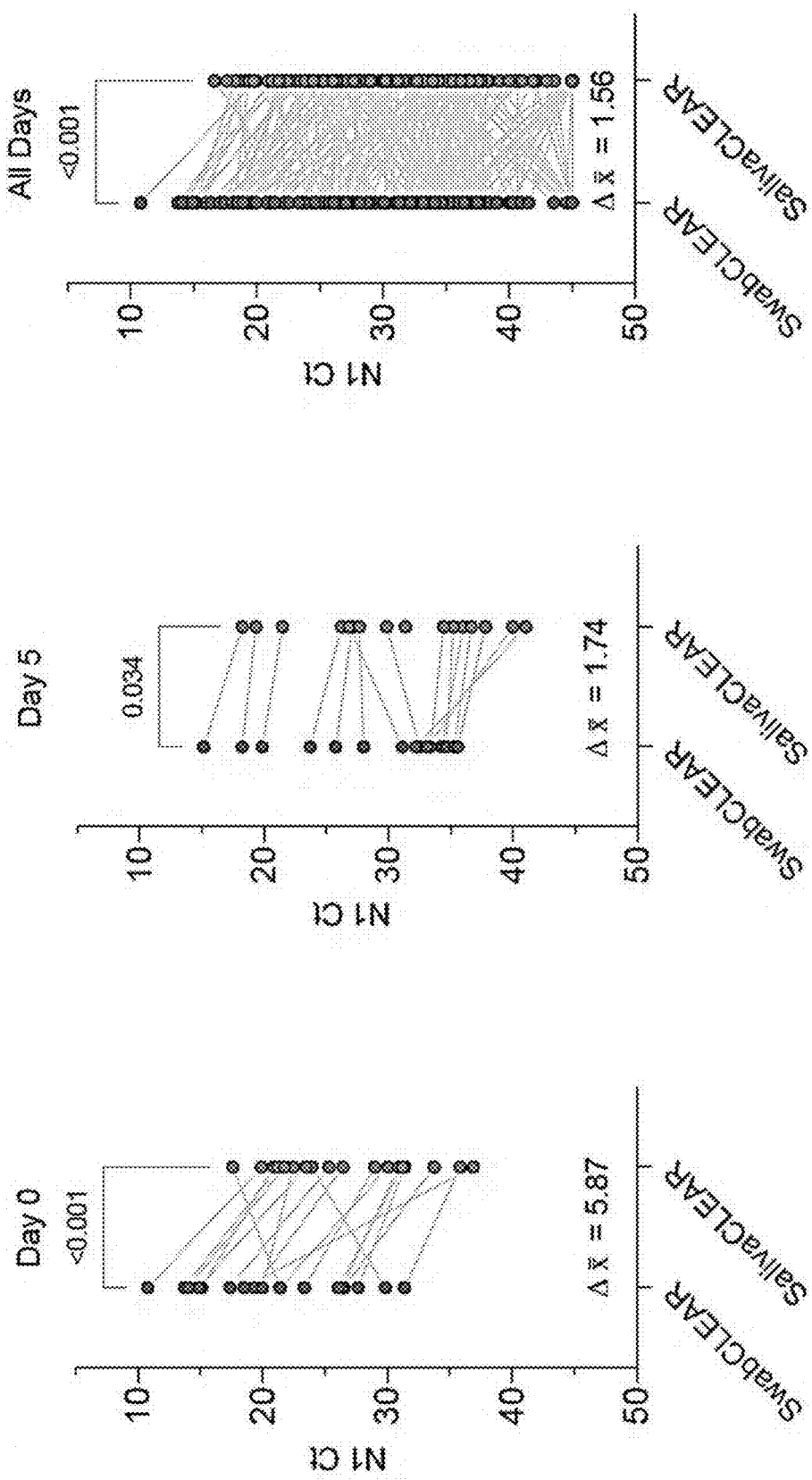

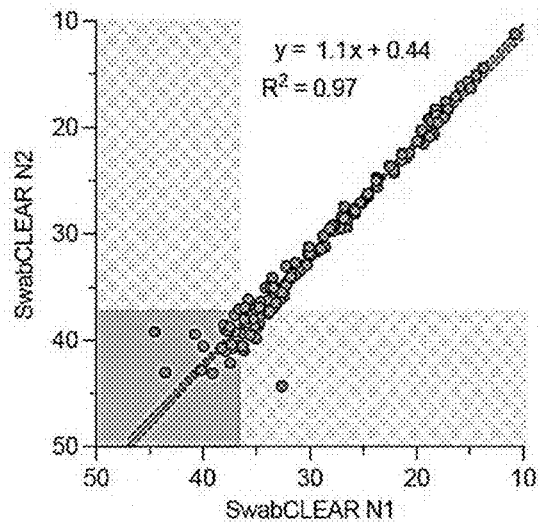
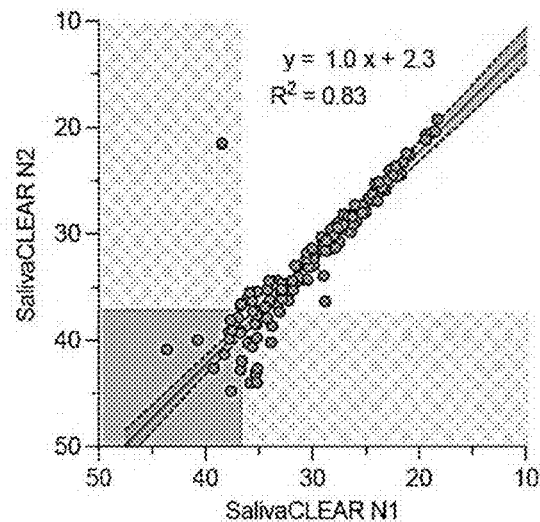
FIG. 11A  FIG. 11B
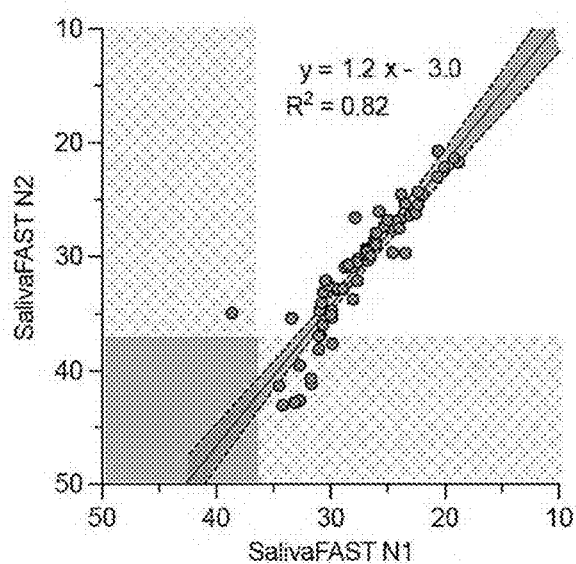
FIG. 11C

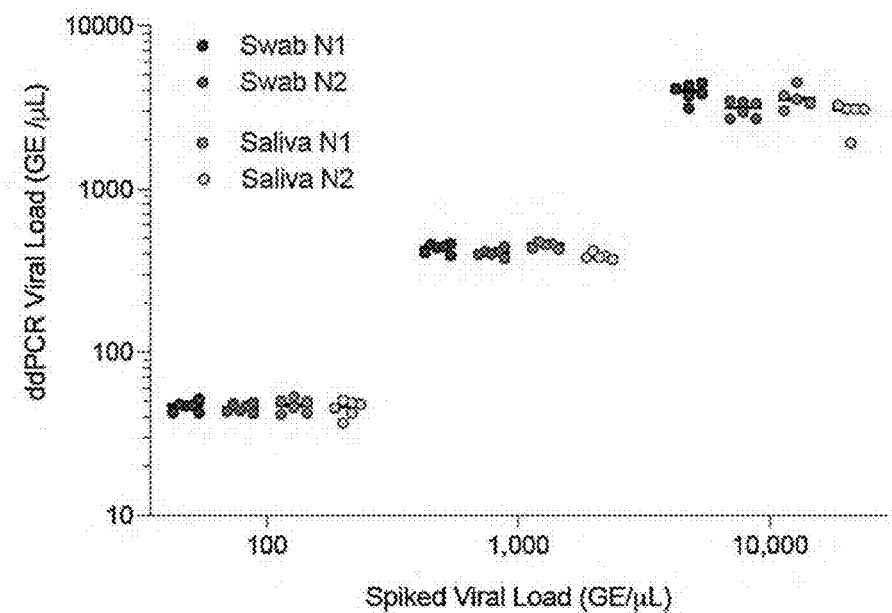
FIG. 12A
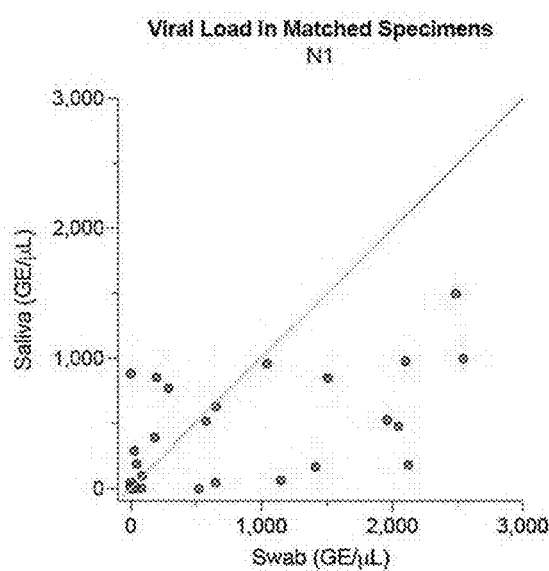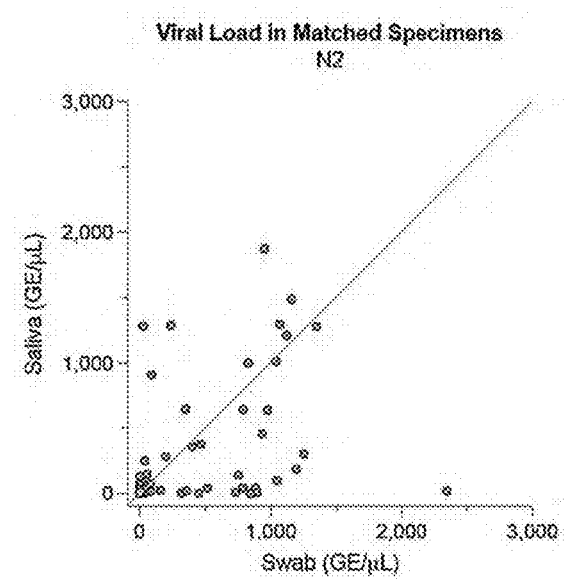
FIG. 12B     FIG. 12C

Clinical Laboratories

The results of tests performed by clinical laboratories nationwide are summarized below. Data from clinical laboratories (the percentage of specimens tested that are positive for influenza) are used to monitor whether influenza activity is increasing or decreasing.

| | Week 4 | Data Cumulative since October 3, 2021 (Week 40) |
|---|---|---|
| No. of specimens tested | 57,889 | 1,442,367 |
| No. of positive specimens (%) | 994 (1.7%) | 37,514 (2.6%) |
| *Positive specimens by type* | | |
| Influenza A | 964 (97.0%) | 36,644 (97.7%) |
| Influenza B | 30 (3.0%) | 870 (2.3%) |

FIG. 16

| Target | Concentration (copies/ul) | Replicates |
|---|---|---|
| Influenza A | 5 | 20/20 |
| Influenza B | 3 | 20/20 |
| SARS-CoV-2 | 10 | 10/10* |

*tentative, need 20 replicates

FIG. 19

EXTRACTION-FREE PATHOGEN TESTING METHODS

CROSS-REFERENCE TO RELATED APPLICATIONS

This application claims priority to, and the benefit of, U.S. Provisional Application No. 63/158,685, filed Mar. 9, 2021, and U.S. Provisional Application No. 63/277,061, filed Nov. 8, 2021, the content of each of which is incorporated by reference herein in its entirety.

TECHNICAL FIELD

The invention generally relates to diagnostic methods, and, more particularly, to compositions and methods for performing extraction-free pathogen testing and detection.

BACKGROUND

The global spread of infectious diseases presents a major healthcare challenge. For example, the rapid spread of the severe acute respiratory syndrome coronavirus-2 (SARS-CoV-2), resulting in a global pandemic, has placed an emphasis on the criticality of rapid and early detection.

Current detection techniques for many infectious diseases involve the use of polymerase chain reaction (PCR). PCR is a technique used to selectively amplify a specific region of DNA of interest (the DNA target). For example, various real-time PCR assays (also referred to as quantitative PCR (qPCR)) for detecting SARS-CoV-2 RNA have been developed worldwide, with different targeted viral genes or regions.

While current PCR methods allow for the detection and diagnosis of infectious diseases, those methods suffer from drawbacks. One notable drawback is that current approaches rely on an initial step of isolating and purifying nucleic acids from a clinical sample as part of the viral testing protocol. For example, the application of qPCR for the relative quantification of an RNA typically requires: (1) the isolation and purification of total RNA from the sample; (2) elution and possible concentration of the material; and (3) the use of purified RNA in a reverse-transcription (RT) reaction resulting in complementary DNA (cDNA), which is then utilized for the qPCR reaction.

The initial nucleic acid isolation and purification step (i.e., extraction step) required in conventional methods, prior to undergoing PCR, constitutes a major bottleneck in the diagnostic process, as it remains both manually laborious and expensive, and further increases the chances of accidental contamination and human error. Furthermore, in a period of high demand, a shortage of nucleic acid extraction supplies can exacerbate the limitations of such viral detection methods.

SUMMARY

The present invention provides compositions and methods for rapid, extraction-free detection and analysis of nucleic acid in a biological sample. More specifically, the invention provides compositions for processing a biological sample and providing usable nucleic acid for subsequent amplification and/or detection (for example, using next generation sequencing technologies), while eliminating the need for an initial nucleic acid extraction step. Moreover, compositions of the invention eliminate the need for viral transport media, which typically inhibit PCR. Compositions of the present invention include, for example, a unique buffer composition for sample transport and preparation that, when mixed with a sample of interest, is capable of preparing nucleic acid from the sample for direct amplification and analysis without the need for initial nucleic acid extraction (i.e., isolation and purification of the nucleic acid).

According to the invention, sample testing is direct from sample without nucleic acid extraction steps. Instead, after clinical samples are provided in a unique buffer composition, nucleic acid is used directly for downstream qPCR, rtPCR, and/or NGS-based diagnostic testing. The invention is useful for the detection of DNA or RNA as required for detection of a particular pathogen. The target nucleic acid for detection may be a human, pathogen or parasitic sequence.

In a preferred embodiment, compositions and methods of the present invention improve upon conventional pathogen testing and detection approaches by reducing the number of steps required for sample preparation and testing. In turn, the time required for viral testing is greatly reduced, resulting in faster turnaround times and delivery of results. Furthermore, the present invention reduces the cost of labor and consumables, while further reducing cross contamination of samples as well as infections of the samples to operators.

The invention is applicable to any pathogen or combination of pathogens. Thus, the invention is useful for the detection of viral nucleic acid, bacterial nucleic acid, or other pathogen-derived sequences (e.g., from parasites, fungi, protozoa, etc.). As described below, the invention provides buffers that are tailored to the detection and/or identification of nucleic acid from different pathogens. In addition, the invention contemplates the detection of multiple pathogen types in a single assay. For example, methods of the invention allow for detection of multiple respiratory viruses (e.g., influenza and SARS) in a single sample.

In one aspect, a method of detecting a viral infection is provided. Methods of the present invention are useful for the detection of viral, bacterial, and other infections, including but not limited to, influenza and parainfluenza viruses, severe acute respiratory syndrome (SARS) virus, respiratory syncytial virus (RSV), rhinoviruses, measles, mumps, adenoviruses, coronaviruses, HPV, HIV, herpes viruses (HSV), Epstein-Barr virus (EBV), hepatitis B virus (HBV), hepatitis C virus (HCV), Merkel Cell polyomavirus (MCV), cytomegalovirus, streptococcal bacteria, bacterial influenza (e.g., *Haemophilus influenzae*), *Chlamydophia pneumoniae*, *Legionella pneumophila*, sexually-transmitted bacterial infections (e.g., chlamydia, gonorrhea, syphilis), tuberculosis, *Helicobacter Pylori*, fungi (e.g., *Aspergillus, Candida albican*), and Mycoplasma pneumoniae, and parasites (e.g., *Trichomonas vaginalis*). Exemplary methods include obtaining a biological sample from an individual. The invention avoids conventional approaches that require nucleic acid extraction steps. Clinical samples are provided in a unique buffer composition in which nucleic acid is directly used for downstream qPCR, rtPCR, or NGS-based diagnostic testing. The invention is useful for the detection of DNA or RNA as required depending on the sample. For purposes of the invention, the target nucleic acid may be a human genomic sequence, a human transcript sequence, any pathogen sequence (viral, bacterial, etc.), a fungal sequence, or a parasitic sequence.

The invention is applicable for use with any biological sample (e.g., any tissue or body fluid sample). Most notably, the sample is a saliva sample (collected via having patients spit into an appropriate collection vessel) or respiratory mucosa (collected via nasopharyngeal or throat swabs).

However, samples also include blood, urine, cerebrospinal fluid, pus, stool, genital secretions, including vaginal secretions, breast nipple aspirates, sweat, lacrimal fluids, needle biopsy fluids, and other excretory samples. For example, when testing for certain viral infections, particularly those infections associated with sexually transmitted infections (STI), the biological sample may be collected by conventional means. In particular, when performing tests for the detection of human papillomavirus (HPV), a biological sample (i.e., tissue and/or bodily fluid) from a subject's anus and/or genitals may be collected via a swab or the like. The primary means for collection include fluid sample (e.g., saliva and/or other secretions) or swabbing (e.g., nasopharyngeal swabs).

Preferred methods further include mixing the sample with an inventive buffer composition that is capable of preparing nucleic acid from the biological sample suitable for nucleic acid amplification without initial extraction of the nucleic acid. Upon mixing the biological sample with the buffer, the buffer allows for nucleic acid in the sample to be readily available for subsequent nucleic acid analysis (i.e., amplification via PCR) without requiring the typical extraction (isolation and purification) step. The buffer composition is generally specific to the type of sample. For example, when testing a saliva sample, the buffer composition includes nuclease-free water, an antifungal solution, an antibiotic solution, a ribonuclease inhibitor, and a reducing agent solution. When testing a nasopharyngeal sample, the buffer composition includes nuclease-free water, an antifungal solution, an antibiotic solution, a ribonuclease inhibitor, and a Tris-Borate-EDTA buffer solution. Furthermore, the buffer composition for a nasopharyngeal sample also serves as a transport medium, in which the swab is immediately placed within an appropriate collection vessel containing the buffer composition. Buffer for bacterial and fungi samples may optionally not use antibiotic and/or antifungal components. However, the presence of, for example, an antibiotic in the buffer does not preclude the extraction-free analysis of bacterial nucleic acids, as the antibiotic is intended to act against bacterial cells and not bacterial nucleic acid.

Methods further include performing one or more PCR assays on the prepared nucleic acid to detect viral, bacterial, or other pathogen-derived nucleic acid, upon which the patient can be diagnosed as having been infected. The step of performing PCR assays includes using viral nucleic acid specific primer-probe sets. In some embodiments, the viral nucleic acid specific primer-probe sets target one or more of the virus's N, ORF1ab, and E genes. Furthermore, in some embodiments, the step of performing the PCR assays includes using a primer-probe set specific to ribonuclease P (RNP). Extraction methods disclosed herein are also useful for detecting human genomic or RNA sequences, as methods are agnostic as to the source of nucleic acid.

In some embodiments, methods further include quantifying the viral nucleic acid. For example, performing the one or more PCR assays includes performing at least one of quantitative PCR (qPCR) and digital PCR (dPCR), which may include droplet digital PCR (ddPCR). In addition to diagnosing the patient, the method may further include the step of determining the severity of the viral infection based on the viral nucleic acid quantity. In some embodiments, methods may further include the step of comparing viral nucleic acid quantities in a plurality of biological samples obtained from the patient at successive time points and determining disease progression based on increases or decreases in the viral nucleic acid quantities over time. Methods of the invention may further include predicting disease outcomes based on the identity or quantity of viral nucleic acid. Methods of the invention may also be used to inform a course of treatment or prognosis. For example, results can be used to determine an appropriate therapeutic or clinical procedure.

In some embodiments, methods of detecting multiple analytes from the same sample are provided. In particular, in some embodiments, multiple viral infections are detected in the same biological sample in accordance with extraction-free, direct-PCR techniques described herein. For example, methods of the present invention may be used to detect a coronavirus infection, such SARS-CoV-2 while also detecting another respiratory pathogen, such as influenza viruses. In other embodiments, a combination of viral, bacterial, and/or other infections can be detected from the same biological sample, including but not limited to, respiratory viruses, influenza and parainfluenza viruses, respiratory syncytial virus (RSV), rhinoviruses, measles, mumps, adenoviruses, coronaviruses, HPV, HIV, herpes viruses (HSV), cytomegalovirus, streptococcal bacteria, bacterial influenza (e.g., *Haemophilus influenzae*), *Chlamydophia pneumoniae*, *Legionella pneumophila*, sexually-transmitted bacterial infections (e.g., chlamydia, gonorrhea, syphilis), tuberculosis, *Helicobacter Pylori*, fungi (e.g., *Aspergillus, Candida albican*), and Mycoplasma pneumoniae, and parasites (e.g., *Trichomonas vaginalis*).

BRIEF DESCRIPTION OF THE DRAWINGS

(FIG. 7D) and −80° C. (FIG. 7E) although this did not impact clinical sensitivity.

FIGS. 9A, 9B, 9C, 9D, 9E, 9F, 9G, and 9H are charts and graphs illustrating the impact of biospecimen type on RT-qPCR-based detection of SARS-CoV-2. The positive and negative agreement between matched nasal swab samples (SwabCLEAR) and saliva samples (SalivaCLEAR) following RNA extraction was assessed for high viral load nasal swab samples with a Ct<30 (FIG. 9A) and low viral load-nasal swab samples Ct=30-35 (FIG. 9B). A comparison of N1 Ct values from matched SwabCLEAR and SalivaCLEAR samples demonstrated lower viral load in saliva at day 0 (FIG. 9C), day 5 (FIG. 9D), and all timepoints during longitudinal monitoring (FIG. 9E). There was moderate correlation between N1 Ct values (FIG. 9F) and N2 Ct values (FIG. 9G) for SwabCLEAR and SalivaCLEAR. RNP values are consistent for SwabCLEAR and SalivaCLEAR (FIG. 9H).

FIGS. 11A, 11B, and 11C are graphs illustrating a comparison of the performance of the methods of the present invention for N1 and N2. There is excellent correlation between Ct values for N1 and N2 for SwabCLEAR (FIG. 11A), SalivaCLEAR (FIG. 11B), and SalivaFAST (FIG. 11C) and negligible additional clinical sensitivity addedby N2.

FIGS. 12A, 12B, 12C, 12D, 12E, 12F, 12G, 12H, and 12I are graphs illustrating the evaluation of viral load according to RT-qPCR and ddPCR. As shown, there is excellent precision and systematic reduction in accuracy in viral load assessment by ddPCR of RNA extracts from both nasal swab and saliva samples (FIG. 12A). The viral loads of matched nasal swab and saliva specimens are compared according to N1 (FIG. 12B) and N2 (FIG. 12C). The performance of N1 and N2 is compared in individual nasal swab (FIG. 12D) and saliva samples (FIG. 12G). The N1 signal in RT-qPCR and ddPCR demonstrated a strong linear relationship for Ct values less than 30 (FIGS. 12E and 12H). At low SARS-CoV-2 concentrations (<100 GE/μL) Ct values in nasal swab (FIG. 12F) and saliva (FIG. 12I) do not correlate with viral load.

FIG. 16 shows summarized results of tests performed by clinical laboratories nationwide for detection of influenza virus.

FIG. 19 is a chart showing a Limit of Detection (LoD) determination using twenty replicates of influenza A and influenza B and 10 replicates of SARS-CoV-2 contrived samples at concentrations ranging from 3 to 10 copies/μL.

DETAILED DESCRIPTION

Figure 1:
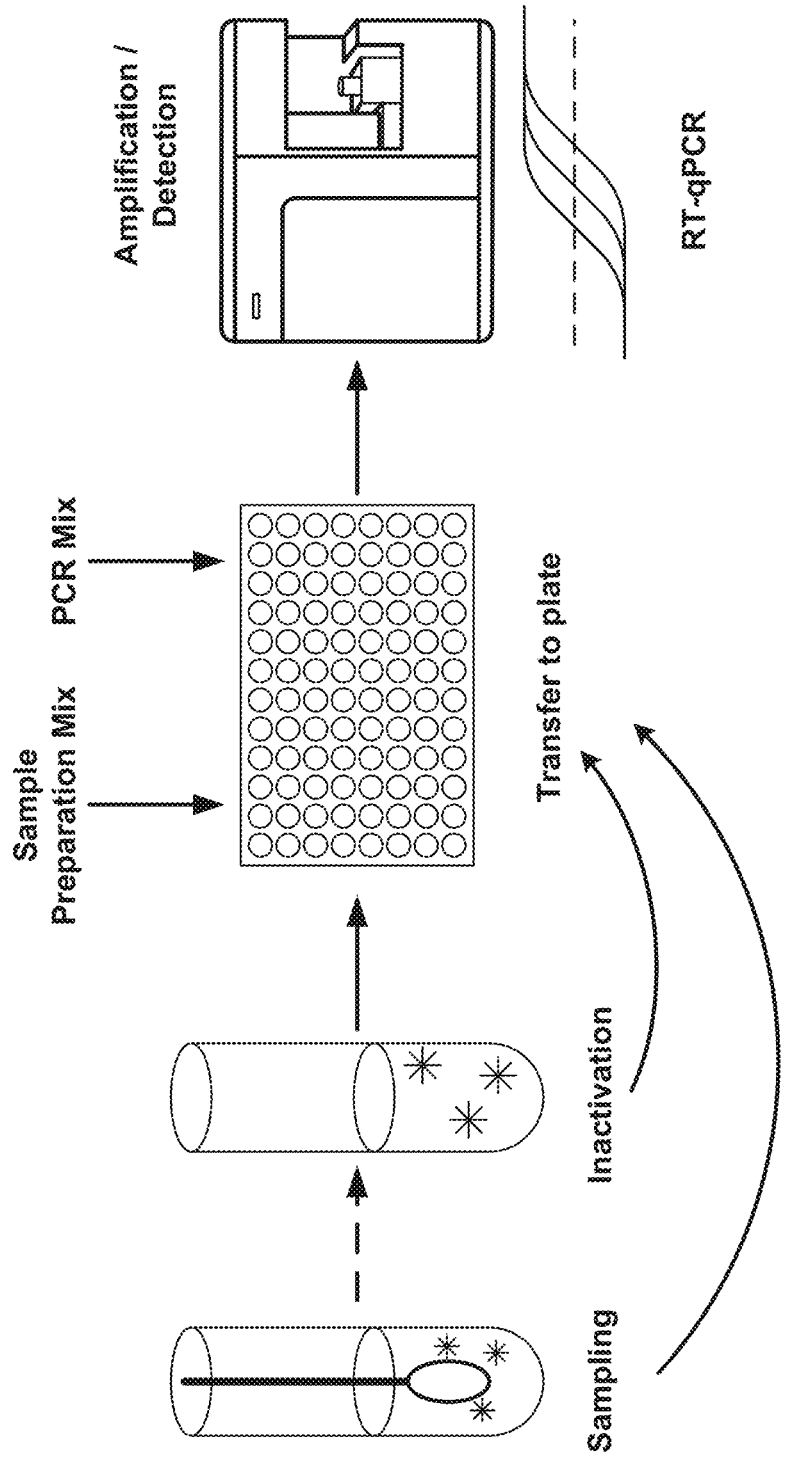
FIG. 1 shows a schematic overview of an extraction-free, real-time RT-qPCR test intended for the qualitative detection of nucleic acid from SARS-CoV-2 in biological specimens (spit or swab samples) collected and processed via unique buffer compositions of the present invention.

The present invention provides compositions and methods allowing for rapid diagnosis of infectious diseases via extraction-free, direct PCR techniques. More specifically, the invention provides compositions for processing a biological samples and providing usable DNA for subsequent PCR assays, while eliminating the need for an initial RNA extraction step. Compositions of the present invention include a unique buffer for sample transport and preparation that, when mixed with a sample of interest, allows nucleic acid from the sample to be directly used for nucleic acid amplification and analysis without the need for initial nucleic acid extraction (i.e., isolation and purification of the nucleic acid). Accordingly, unlike conventional approaches, which include an RNA extraction step using industrial RNA extraction kits and techniques, the direct sample testing of the present invention circumvents this process by omitting the extraction step.

As a result, compositions and methods of the present invention improve upon conventional pathogen testing and detection approaches by reducing steps and increasing efficiency. The time required for pathogen testing is greatly reduced, resulting in faster turnaround times and delivery of results. Furthermore, the present invention reduces the cost of labor and consumables, while further reducing cross contamination of samples as well as infections of the samples to operators.

It should be noted that methods described herein are useful to diagnose a variety of infectious diseases, including bacterial, fungal, parasitic, or viral. However, for the sake of simplicity and ease of description and example, the following describes methods for diagnosing SARS-CoV-2 via extraction-free direct PCR approaches. The same procedures are useful for bacterial, fungal or parasitic infections.

The exemplary pathogen, SARS-CoV-2, is a virus identified as the cause of an outbreak of respiratory illness (referred to as coronavirus disease 2019 (COVID-19)) resulting in severe symptoms and deaths. Asymptomatic spread is common with SARS-CoV-2. Accordingly, to monitor the presence of SARS-CoV-2 and to prevent its spread, it is crucial to detect infection as early and as fast as possible. Methods of the present invention provide rapid detection of a viral infection (i.e., presence of the virus in a patient) by reducing the number of steps during sample preparation that are typically required with conventional viral detection methods relying on PCR assays.

In general, workflow for use of the invention comprises obtaining a biological sample from an individual suspected of being infected. The method of sample collection, as well as the type of sample collected, may depend on the specific disease to be tested. For example, the biological sample may include a body fluid and may be collected in any clinically-acceptable manner. The fluid sample is generally collected from a patient either exhibiting symptoms or suspected of having contact with others that have tested positive for the disease.

A body fluid may be a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CSF. A sample also may be media containing cells or biological material. A sample may also be a blood clot, for example, a blood clot that has been obtained from whole blood after the serum has been removed. In certain embodiments, the sample is blood, saliva, or semen collected from the subject.

For SARS-CoV-2, a biological sample is generally collected via a nasopharyngeal or throat swab, or, in some cases, the sample may be saliva. Next, the sample is prepared for subsequent analysis. Preparation of the sample includes mixing the sample with a buffer composition capable of preparing nucleic acid from the biological sample suitable for nucleic acid amplification without initial extraction of the nucleic acid.

As previously noted, current viral testing approaches rely on an initial step of isolating and purifying nucleic acids from a clinical sample as part of the viral testing protocol. For example, the application of qPCR for the relative quantification of an RNA of interest is preceded by: (1) the isolation and purification of total RNA from the sample; (2) elution and possible concentration of the material; and (3) the use of purified RNA in a reverse-transcription (RT) reaction resulting in complementary DNA (cDNA), which is then utilized for the qPCR reaction. The initial nucleic acid isolation and purification step (i.e., extraction step) required in current methods, prior to undergoing PCR, constitutes a major bottleneck in the diagnostic process, as it remains both manually laborious and expensive, and further increases the chances of accidental contamination and human error.

Polymerase chain reaction (PCR) refers to methods by K. B. Mullis (U.S. Pat. Nos. 4,683,195 and 4,683,202, incorporated herein by reference). Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. Amplification or sequencing adapters or barcodes, or a combination thereof, may be attached to the fragmented nucleic acid. Such molecules may be commercially obtained, such as from Integrated DNA Technologies (Coralville, IA). In certain embodiments, such sequences are attached to the template nucleic acid molecule with an enzyme such as a ligase. Suitable ligases include T4 DNA ligase and T4 RNA ligase, available commercially from New England Biolabs (Ipswich, MA). The ligation may be blunt ended or via use of complementary overhanging ends.

Digital polymerase chain reaction (dPCR) is a refinement of conventional polymerase chain reaction methods that can be used to directly quantify and clonally amplify nucleic acids strands including DNA, cDNA, or RNA. In dPCR a sample is separated into a large number of partitions and the reaction is carried out in each partition individually, thereby permitting sensitive quantification of target DNA through fluorescence analysis in each partition as opposed to a single value for the entire sample as found in standard PCR techniques.

Droplet Digital PCR (ddPCR) is a method of dPCR wherein the aforementioned partitions consist of nanoliter-sized water-oil emulsion droplets in which PCR reactions and fluorescence detection can be performed using, for example, droplet flow cytometry. The methods for creating and reading droplets for ddPCR have been described in detail elsewhere (see Zhong et al., 'Multiplex digital PCR: breaking the one target per color barrier of quantitative PCR', Lab Chip, 11:2167-2174, 2011), but in essence each droplet is like a separate reaction well and, after thermal cycling, the fluorescence intensities of each individual droplet were read out in a flow-through instrument like a flow cytometer that recorded the peak fluorescence intensities.

While compositions and methods of the invention may be used to detect nucleic acid specific to any pathogen, in preferred embodiments, a respiratory pathogen is the detection target. Exemplary primers and probes for the detection of respiratory pathogens, such as SARS-CoV-2, have been disclosed (see, e.g., Tao S, et al., 2020 and Dong, I et al. 2020). Compositions and methods of the invention for the detection of COVID-19 infection using ddPCR of saliva and nasopharyngeal samples contemplate using the same primers and probes discussed therein. Furthermore, in some embodiments, the step of performing the one or more PCR assays includes using a primer-probe set specific to ribonuclease P (RNP).

For example, the primers and probes used with the methods of the present invention may include those primers and probes listed and associated with the CDC 2019-nCoV Real-Time RT-PCR Diagnostic Panel (as published on CDC website at: https://www.cdc.gov/coronavirus/2019-ncov/lab/rt-per-panel-primer-probes.html, last updated Jun. 6, 2020). In the present invention, such primers and probes may include, but are not limited to, SARS-CoV-2 Research Use Only qPCR Primers & Probes offered by Integrated DNA Technologies (IDT). For example, such primers/probes include: nCOV_N1 Forward Primer (catalog number 10006830); nCOV_N1 Reverse Primer (catalog number 10006831); nCOV_N1 Probe (catalog number 10006832); RNase P Forward Primer (catalog number 10006836); RNase P Reverse Primer (catalog number 10006837); and RNase P (ATTO™ 647) Probe (catalog number 10007062).

In addition to diagnosing an individual as having been infected with a virus, inventive methods may further include the step of determining the severity of the viral infection based on the viral nucleic acid quantity. For example, methods of the invention are useful to assess viral load, which can be directly correlated with disease severity and/or progression. In some embodiments, methods may further include the step of comparing viral nucleic acid quantities in a plurality of biological samples obtained from the patient at successive time points and determining disease progression based on increases or decreases in the viral nucleic acid quantities over time. Methods of the invention can also be used to predict disease outcomes and/or severity based on the viral nucleic acid quantity. The disease outcomes are selected from one or more of intubation, ICU admission, discharge, time until intubation, time until discharge, and death.

FIG. 1 shows a schematic overview of an extraction-free, real-time RT-qPCR test intended for the qualitative detection of nucleic acid from SARS-CoV-2 in biological specimens (spit or swab samples) collected and processed via unique buffer compositions of the present invention. In the case of a nasopharyngeal swab, the swab is used for the collection of respiratory mucosa and then placed within an acceptable vessel which includes a unique buffer composition of the present invention, used as both a transport medium and sample preparation medium for the potential SARS-CoV-2 viral particles. In the case of saliva, a patient will simply spit in an acceptable vessel, at which point the saliva will then be transferred to another vessel containing the unique buffer composition for sample preparation. Upon being collected and provided within the unique buffer composition, viral particles may be inactivated either through heating or by direct lysis in the buffer. The inactivated samples can then be used for downstream qPCR diagnostic testing without the need for the additional RNA extraction step (isolation and purification) that conventional approaches rely on. Rather, the prepared sample may be transferred to a PCR-plate (96/384-well) format in which cDNA synthesis by reverse transcription (RT) and detection by qPCR may take place. Accordingly, unlike the widely used approach, which includes an RNA extraction step using industrial RNA extraction kits, direct sample testing circumvents this process by omitting extraction.

Figure 2:
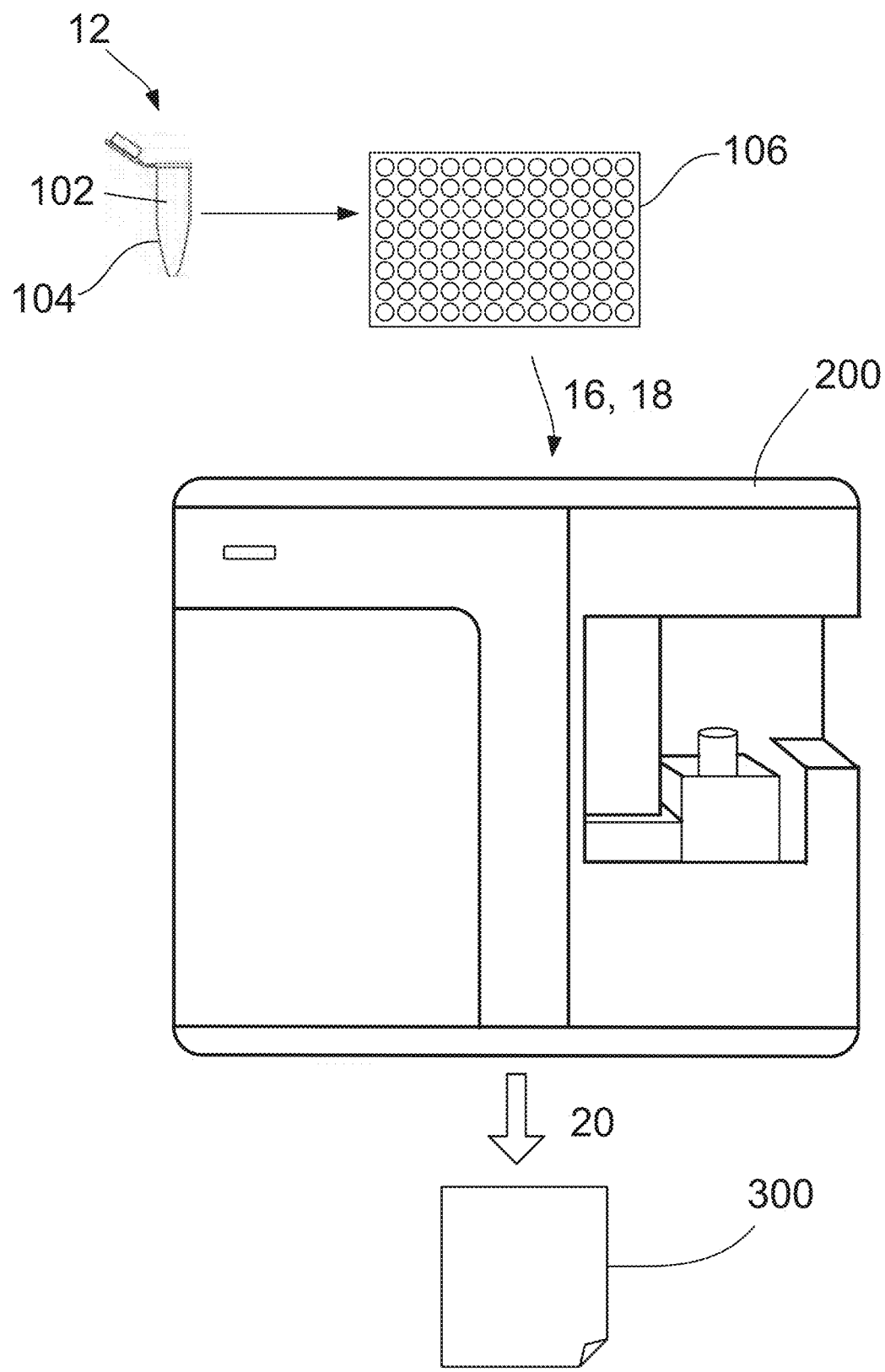
FIG. 2 shows a sample from a patient suspected of having a viral infection and loading of the sample into an instrument capable of performing one or more assays on the sample to determine whether viral nucleic acid associated with the viral infection is present.

FIG. 2 shows a sample 102 that has been collected from a patient suspected of having a viral infection and loading of the sample into an instrument 200 capable of performing one or more assays on the sample to determine whether viral nucleic acid associated with the viral infection is present. As will be described in greater detail herein, the sample 102 (saliva or respiratory mucosa) may be contained within a suitable container 104 that is obtained 12 from a patient suspected of having a viral infection (or having been in close contact with one or more persons having or suspected of having the viral infection). For example, in some embodiments, samples may be collected and stored in their own container, such as a centrifuge tube such as the screw cap cryovial. Preferably a 1.9 ml cryovial with screw cap is used. A funnel or saliva collection aid is used to facilitate saliva collection, and a nasal swab with a proximal breakpoint is used, which allows the swab to be inserted into the tube after use. The advantage of using the same tube for both saliva and nasal swab is to facilitate downstream sample accessioning, automation using, for example, a decapper. The screw cap is important to prevent contamination. The standard size of cryovial is allow direct sample storage without additional sample transfer.

FIG. 2 further illustrates loading of the sample 102 into a PCR-plate 106, in which sample preparation 14 may take place (introduction of the sample to the unique buffer and/or PCR mix), at which point the plate 106 may then be introduced into an instrument 200 capable of performing one or more PCR assays on the sample 102 to determine whether viral nucleic acid associated with the virus is present. In particular, the instrument 200 may be configured to provide any one of the prior steps of method 10, including, but not limited to, detection of viral RNA, reverse transcribing of RNA to produce cDNA, amplification of cDNA (operation 16), analysis of data from the amplification step (operation 18), and generation of a report 300 providing information related to the virus evaluation (operation 20). Accordingly, the instrument 200 is generally configured to detect, sequence, and/or count the target nucleic acid(s) or resulting fragments. In this instance, where a plurality of fragments are present or expected, the fragment may be quantified, e.g., by qPCR. The resulting report 300 may include the specific data associated with the assay, including, for example, patient data (i.e., background information, attributes and characteristics, medical history, tracing information, etc.), test data, including whether the sample tested positive or negative for the virus, and, if positive, further metrics, including disease progression and predicted disease outcome.

Extraction-free PCR relies, in part, on the efficacy of proteinase K (PK) digestion, which would otherwise degrade a desired sample of DNA or RNA. To optimize for PK activity in either a swab or saliva matrix, a variety of buffer components were tested. This is particularly important for swab samples. Unlike saliva, which one is able to collect and transport as raw saliva, swab samples should be stored in viral transport medium (VTM). However, conventional swab samples in VTM usually require RNA extraction for SARS-CoV-2 testing.

The inventors tested a variety of buffer components, VTM, and a commercial swab collection device-OR100

(DNA Genotek) for extraction-free PCR. Negative swab samples were collected from healthy volunteers and put into each solution. Samples then were spiked into heat-inactivated SARS-CoV-2 virus, mixed with PK by aliquoting sample into a 96-well plate pre-filled with either a mix of saliva preparation buffer (see below) and PK (Promega) for saliva samples or PK alone for swab samples. For saliva samples (SalivaFAST), 30 µL from a single saliva sample was mixed with 5 µL saliva preparation buffer and 5 µL PK in each well of the plate. For swab samples (SwabFAST), 35 µL from a single swab sample was mixed with 5 µL PK per well. The prepared sample plate was then placed on a digital microplate shaker at 500 RPM for one minute, then on a thermal cycler at 95° C. for five minutes for heat-inactivation.

Figure 3A:
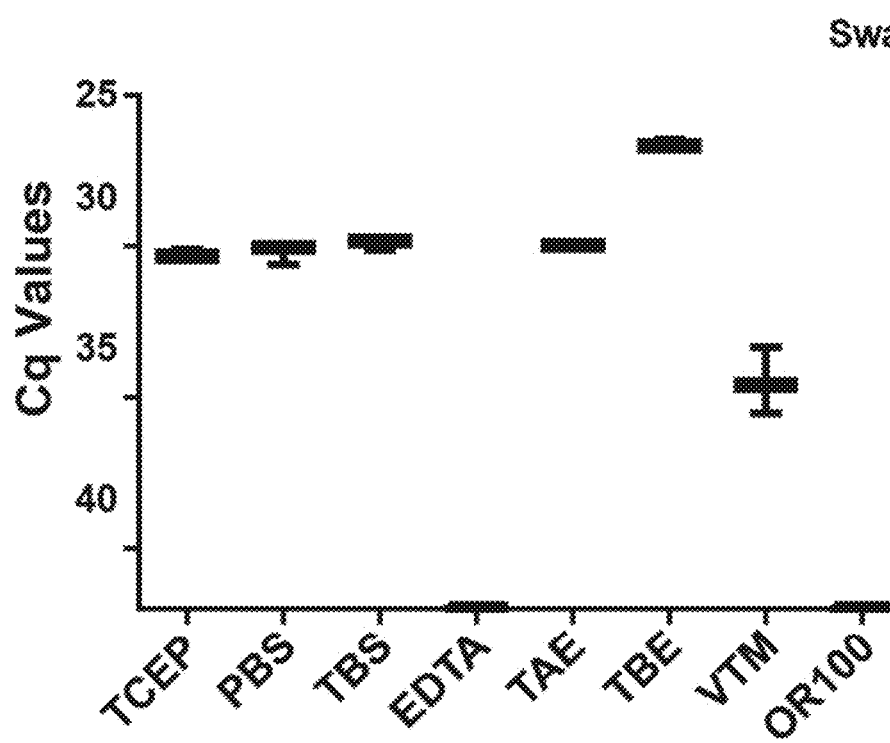
FIGS. 3A and 3B are graphs illustrating the use of different buffer components for the extraction-free RT-qPCR testing of swab and saliva samples (FIG. 3A and FIG. 3B, respectively), in which quantification cycle (Cq) values at N1 primer/probe region are plotted for individual buffer components used.
Figure 3B:
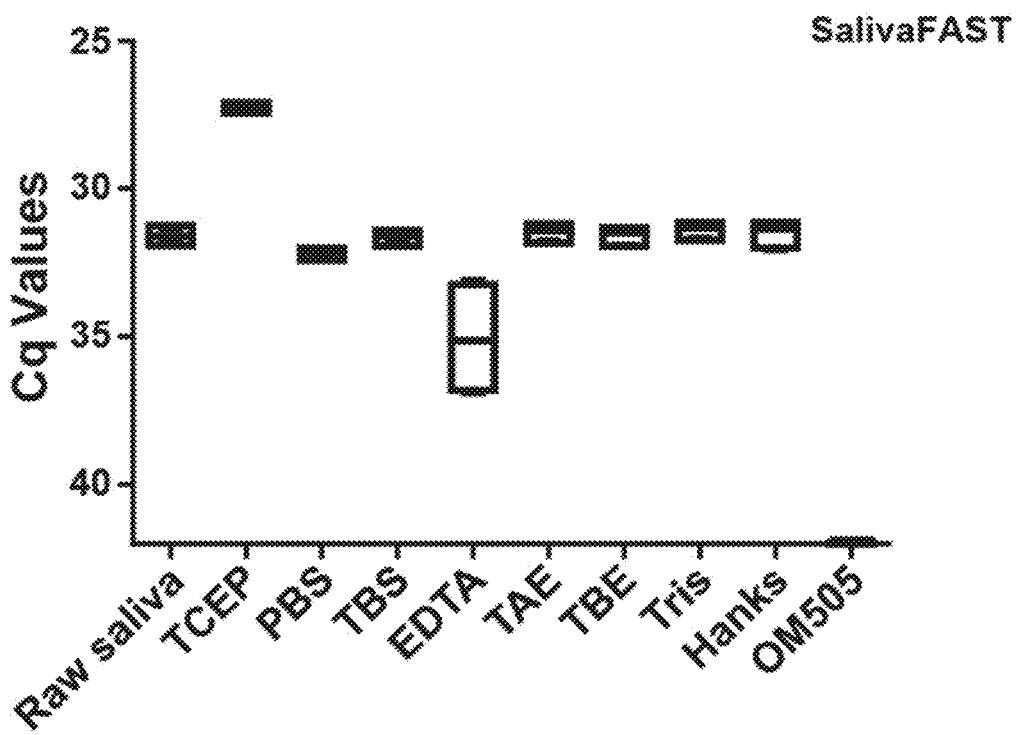

As shown in FIG. 3A, swab samples in PBS, VTM, and OR100 did not generate positive signals at N1 region. Among the positive signals, the contrived swab sample in Tris-Borate-EDTA (TBE) buffer produced the strongest quantification cycle (Cq) value, which comprise the buffer component for the viral transport buffer (VTB) of the invention. Similarly, avariety of buffer components, raw saliva, and a commercial saliva collection device-OM505 (DNAGenotek) were tested for extraction-free PCR. As shown in FIG. 3B, contrived saliva samples in OM505 didn't generate positive signals at N1 region. Among the positive signals, the contrived saliva sample in Tris (2-carboxyethyl) phosphine (TCEP) buffer condition produced the strongest Cq value, which is used to improve PK efficacy in the SalivaFAST protocol.

Stability of Viral Transport Buffer (VTB)

Figure 4A:
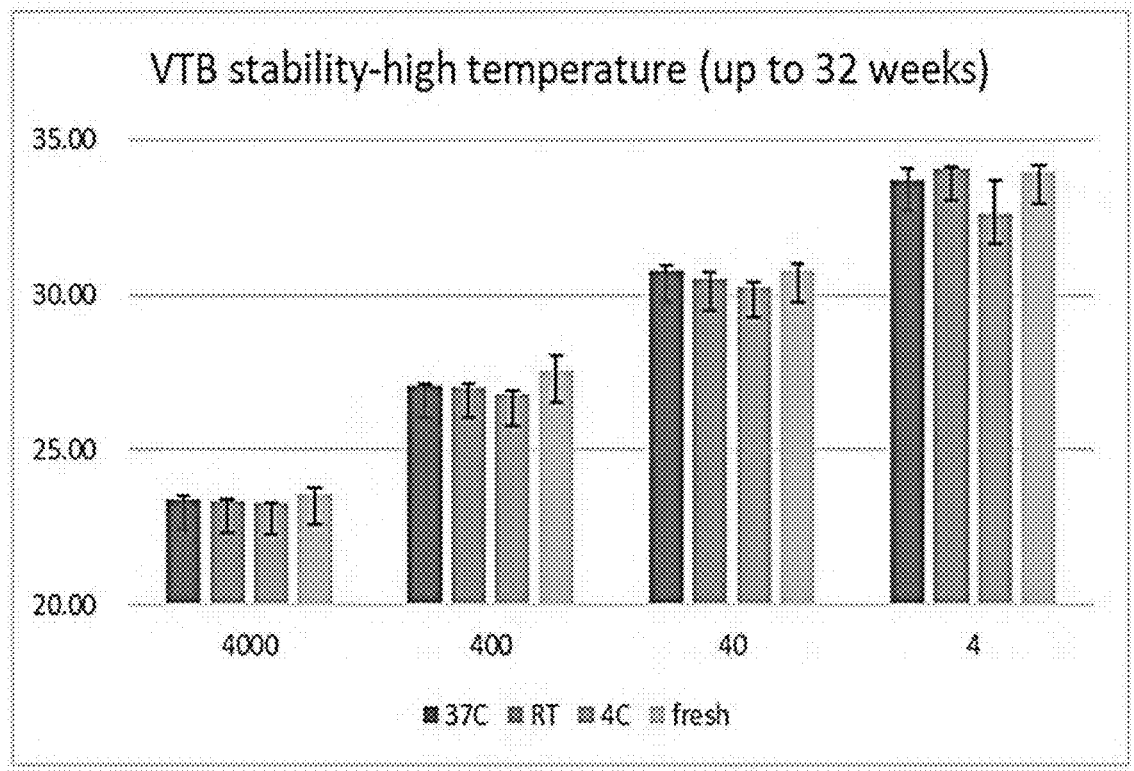
FIGS. 4A and 4B are graphs illustrating stability assays performed on swab samples with the use of a viral transfer buffer (VTB) consistent with the present disclosure, in which VTB was placed at higher temperatures for 32 weeks (FIG. 4A) and low temperatures for up to 3 weeks (FIG. 4B), in which Cq values at N1 primer/probe region are plotted for comparison.
Figure 4B:
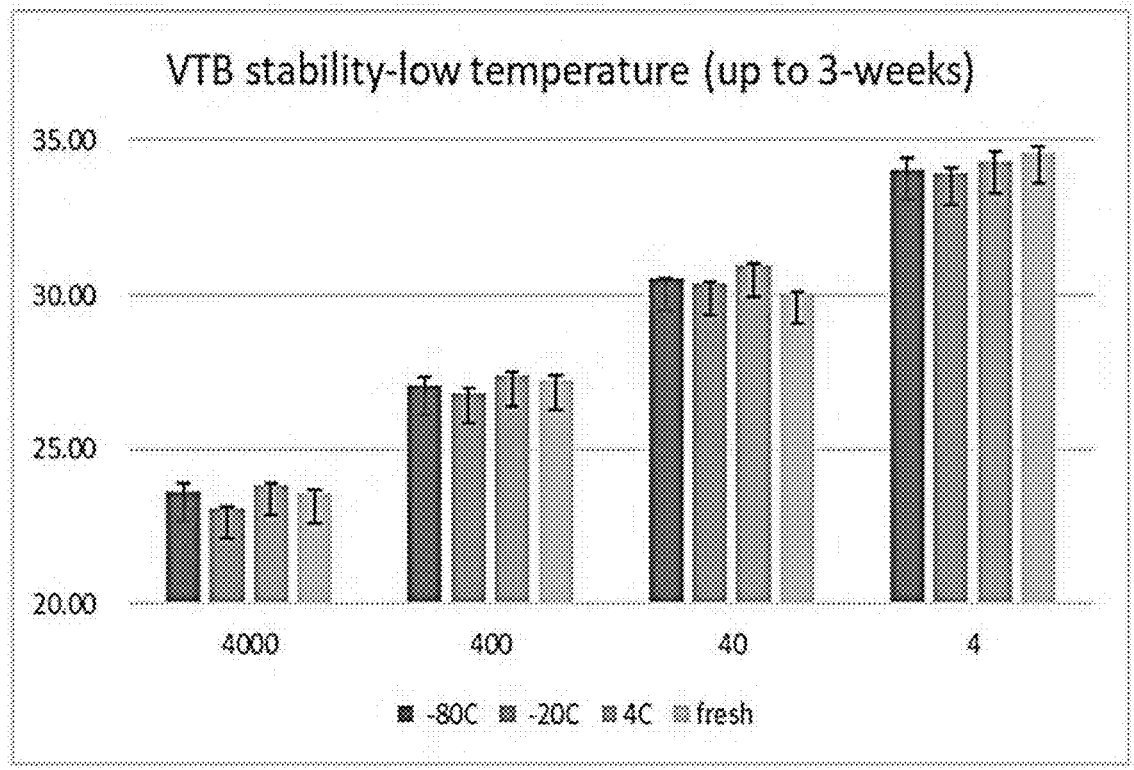
Figure 5A:
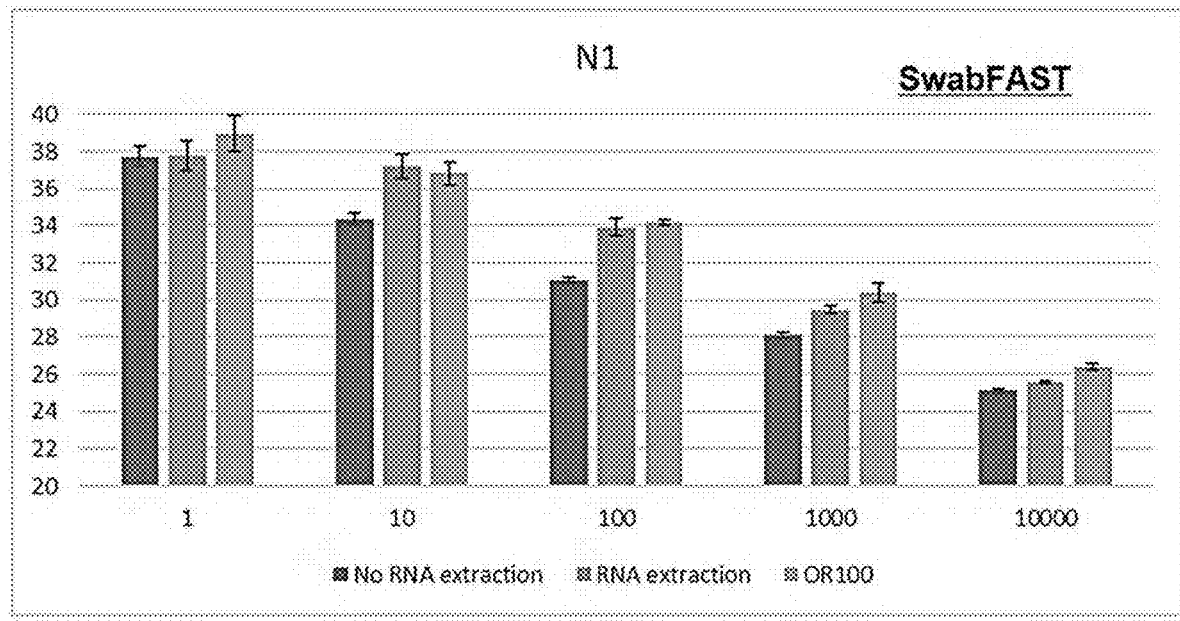
FIGS. 5A, 5B, 5C, and 5D are graphs comparing test performance based on RNA extraction and extraction-free methods consistent with the present disclosure performed on swab samples (see FIGS. 5A and 5C) and saliva samples (see FIGS. 5B and 5D), in which Cq values at N1 primer/probe region (see FIGS. 5A and 5B) and at RNP gene (see FIGS. 5C and 5D) are plotted for comparison.
Figure 5B:
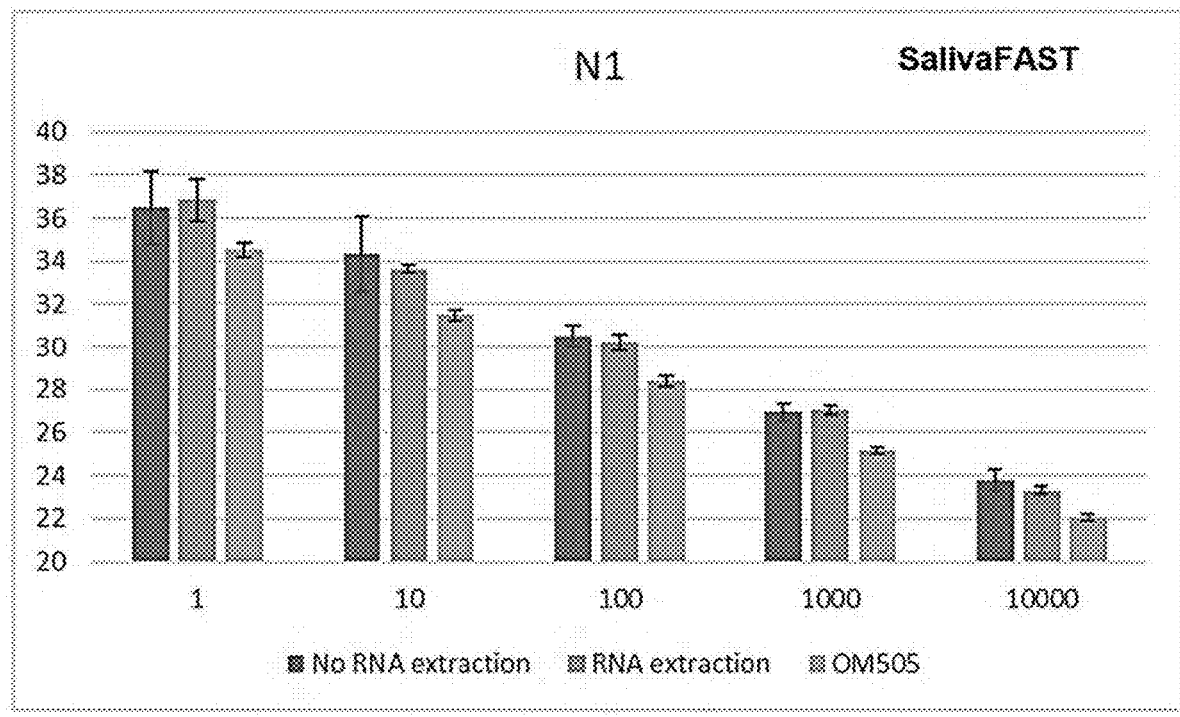
Figure 5C:
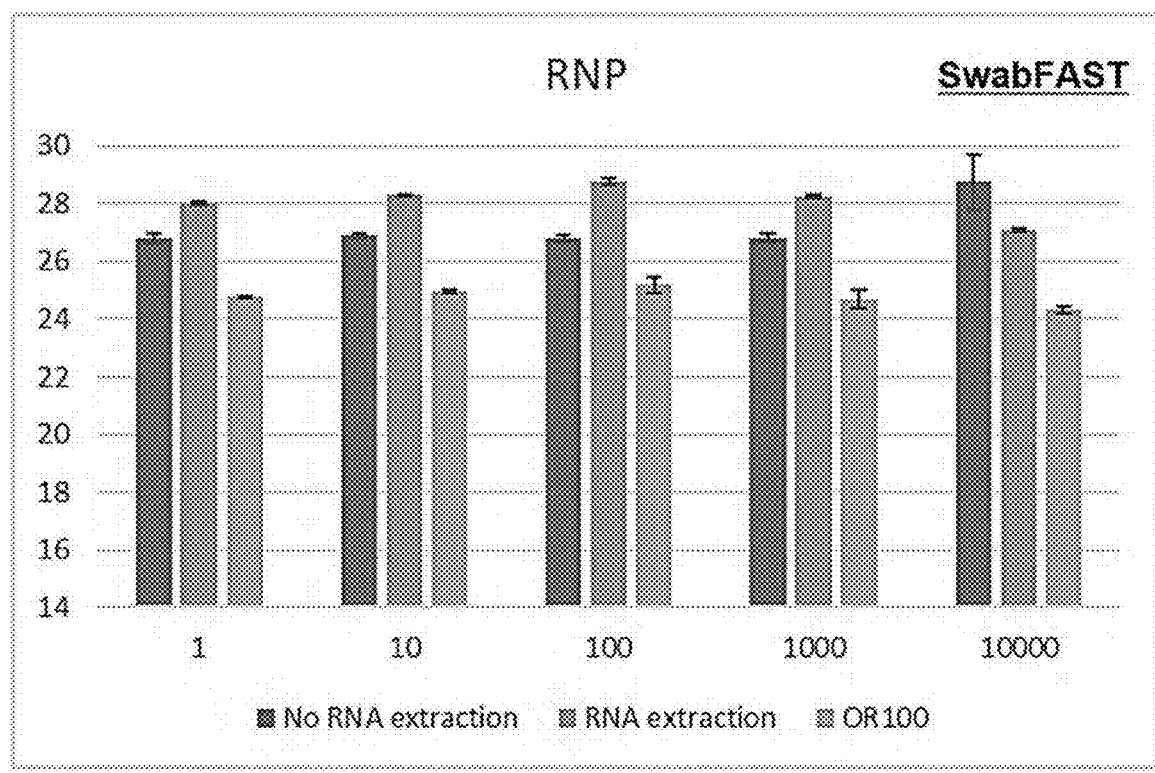
Figure 5D:
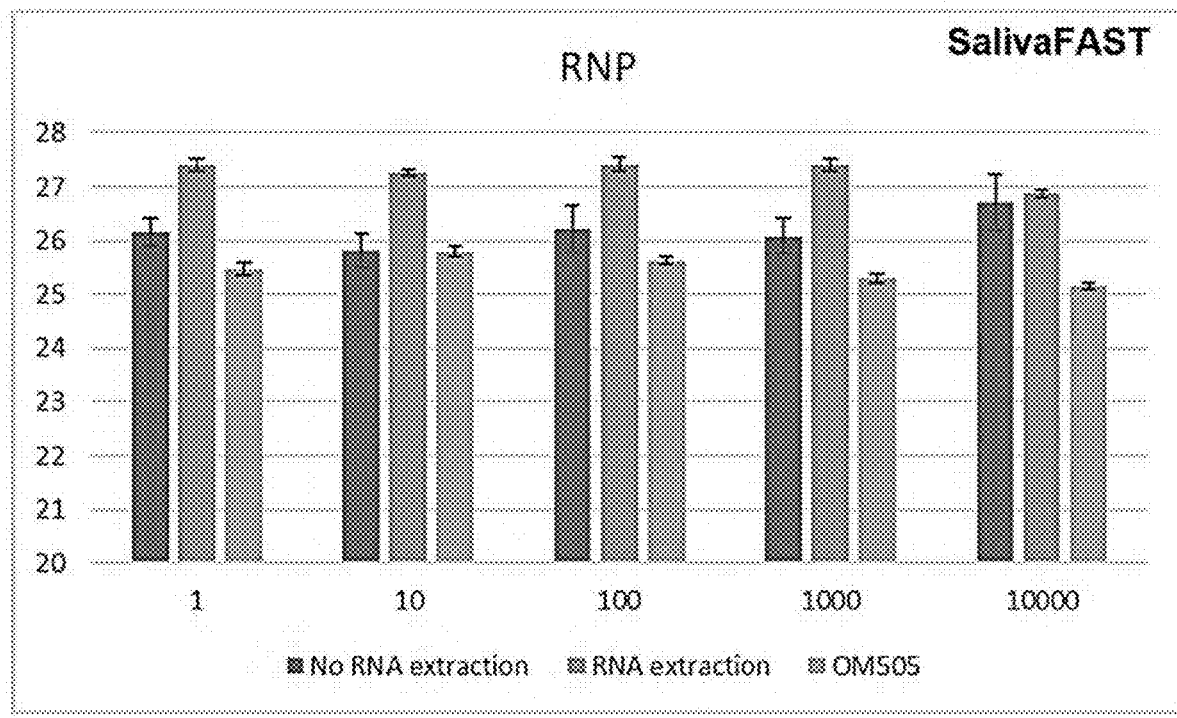

VTB stability was tested at different temperatures and durations. At higher temperatures, VTB was placed at 4° C., room temperature and 37° C. for 32 weeks, negative swab samples were spiked in heat-inactivated SARS-CoV2 virus at different concentrations, and were tested every four weeks. The result at 32 weeks is shown in FIG. 4A. Similarly, at low temperatures, VTB was placed at −80° C., −20° C. and 4° C., for 3 weeks as of this manuscript, negative swab samples were spiked in heat-inactivated SARS-CoV2 virus at different concentrations, and were tested every week. The result at 3 weeks is shown in FIG. 4B. The Cq value at N1 primer/probe for SARS-CoV-2 contrived samples at different concentrations (4, 40, 400, 4000 copies/µL) remained consistent across all the experimental storage temperatures.

Analytical Validation of Extraction-Free PCR Testing

To establish analytical validity of the extraction free RT-qPCR assay for nasal swab and saliva specimens, the results from RT-qPCR testing with or without RNA extraction were compared (see FIGS. 5A-5D). Next, limit of detection (LoD) studies were conducted to determine the lowest detectable concentration of SARS-CoV-2 at which approximately 95% of all true positive samples test positive (see FIGS. 5A, 5B, 5C, and 5D).

RT-qPCR Results with or without RNA Extraction:

As shown in FIGS. 5A, 5B, 5C, and 5D, in an effort to demonstrate that the extraction-free RT-qPCR methods are equivalent to the RT-qPCR methods with RNA extraction in either swab or saliva samples, the following three methods were compared at different SARS-CoV-2 concentrations: (1) contrived samples (swab or saliva) mixed with buffer analyzed without RNA extraction (left vertical bar plot in blue); (2) contrived samples (swab or saliva) analyzed with RNA extraction (middle vertical bar plot in orange); and (3) contrived samples (swab or saliva) collected with DNA Genotek's devices (OR-100 for swab and OM-505 for saliva) analyzed with RNA extraction (right vertical bar plot in gray). The Cq values at the N1 region of SARS-CoV-2 gene (FIGS. 5A and 5B) and RNP gene (FIGS. 5C and 5D) primer/probe for the three methods at each SARS-CoV-2 concentration (1, 10, 100, 1000, 10000 copies/µL) for both-specimen types produce the same qualitative and similar quantitative test results with Cq values across all comparisons.

Figures 6A, 6B:
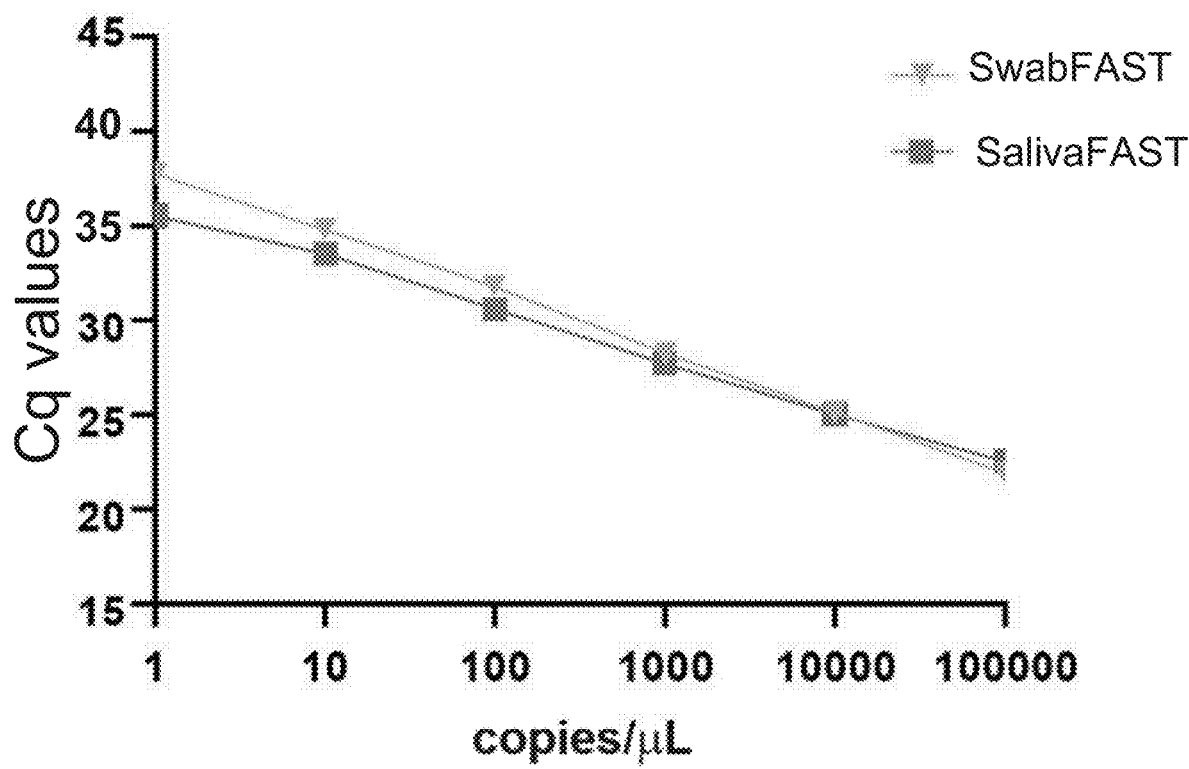
FIG. 6A is a graph illustrating plots of serial dilution curves associated with swab and saliva sample testing methods of the present invention, wherein such curves are plotted using SARS-CoV-2 contrived samples at concentrations ranging from 1 to 100,000 copies/μL. The Cq values at N1 primer/probe region are plotted.
FIG. 6B is a chart showing a Limit of Detection (LoD) determination using six replicates of SARS-CoV-2 contrived samples at concentrations ranging from 0 to 100 copies/μL.

Limit of Detection (LoD):

First, tenfold serially diluted contrived samples at concentration ranging from 1 to 100,000 copies/µL heat-inactivated SARS-CoV-2 viruses were used in independent runs of SwabFAST and SalivaFAST, respectively (see FIG. 6A). The range of LoD was further narrowed using six replicates of serially diluted contrived samples at concentration levels of 0, 2, 4, 6, 8, 10, 50, and 100 copies/µL for each specimen type. A preliminary LoD was identified at 4 copies/µL. Confirmation of the LoD was done with 20 replicates at this concentration level. Results show that the LoD of the assays is established at 4 copies/µL, where over 95% of the replicates were tested positive (20/20) for both swab and saliva (see FIG. 6B).

Clinical Validation of Extraction-Free PCR Testing

RT-qPCR Results with or without RNA Extraction:

SARS-CoV-2 positive and negative clinical samples were tested with or without RNA extraction (COVIDFast). 38 SARS-CoV-2 positive and 31 negative swab samples were split in half and the RT-qPCR assay was run with or without RNA extraction. The positive percent agreement (PPA) and the negativepercent agreement (NPA) are both 100% (see Table 1A below).

TABLE 1A

Comparison of test performance with and without RNA extraction in clinical samples

| | | CDC Protocol RNA Extraction* | | |
|---|---|---|---|---|
| | | +(pos) | −(neg) | |
| SwabFAST RNA Extraction-free* | +(pos) | 38 | 0 | 38 |
| | −(neg) | 0 | 31 | 31 |
| | | 38 | 31 | 69 |

PPA—100%
NPA = 100%

Similarly, 82 SARS-CoV-2 positive and 171 negative saliva samples were split in half and the RT-qPCR assay was run with or without RNA extraction. The PPA and NPA are 98.8% and 99.4% respectively (see Table 1B below).

TABLE 1B

Comparison of test performance with and without RNA extraction in clinical samples

| | | CDC Protocol RNA Extraction* | | |
|---|---|---|---|---|
| | | +(pos) | −(neg) | |
| SalivaFAST RNA Extraction-free* | +(pos) | 81 | 1 | 82 |
| | −(neg) | 1 | 170 | 171 |
| | | 82 | 171 | 253 |

PPA—98.8%%
NPA = 99.4%

Clinical Validation Against Another Extraction-Free Assay (SalivaDirect):

COVIDFast tests were also clinically validated against SalivaDirect. SwabFAST was validated using a paired SalivaDirect test from the same patient, and SalivaFAST was validated using the same saliva sample collected for SalivaDirect. 179 paired clinical samples—i.e., each testing subject provided one saliva sample and oneanterior nares swab sample—from community members were analyzed by SwabFAST and compared to SalivaDirect. The PPA and the NPA are 83.3% and 99.4% respectively (see Table 2A below).

TABLE 2A

Clinical validation of SwabFAST (A) and SalivaFAST (B) against SalivaDirect

|  |  | SalivaDirect | | |
| --- | --- | --- | --- | --- |
| SwabFAST |  | +(pos) | −(neg) |  |
|  | +(pos) | 5 | 1 | 6 |
|  | −(neg) | 1 | 178 | 179 |
|  |  | 6 | 179 | 185 |

PPA—83.3% (5/6)
NPA = 99.4% (178/179)

Similarly, 40 raw saliva clinical samples were analyzed by SalivaFAST and compared to SalivaDirect run by an independent SalivaDirect authorized CLIA lab. The PPA and the NPA are 95% and 100% respectively (see Table 2B below).

TABLE 2B

Clinical validation of SwabFAST (A) and SalivaFAST (B) against SalivaDirect

|  |  | SalivaDirect | | |
| --- | --- | --- | --- | --- |
| SalivaFAST |  | +(pos) | −(neg) |  |
|  | +(pos) | 19 | 0 | 19 |
|  | −(neg) | 1 | 20 | 21 |
|  |  | 20 | 20 | 40 |

PPA—95% (19/20)
NPA = 100% (20/20)

Saliva and Nasal Swab Examples

The following provides exemplary protocols for detection of viral nucleic acid in accordance with methods of the present invention. A biological sample is obtained and may include a human bodily fluid and may be collected in any clinically acceptable manner.

For many respiratory infections, a biological sample is generally collected via a nasal or throat swab, or, in some cases, saliva. In other examples, the sample may include an aerosol sample or droplets obtained in air or, more preferably, via the expulsion of droplets with a cough or sneeze.

Saliva Sample Collection:

Saliva samples may be collected from individuals by, for example, having them spit into a provided sterile container. Saliva collection devices may include, for example, 1.9 ml storage tube or vial with screw cap (externally threaded). The storage tube may further include a barcode or other identifying mark that is a machine-readable label that is useful for tracking and traceability purposes, particularly when sharing data between laboratories, locations, and automation processes. For example, in some embodiments, the storage tube includes a pre-printed 10-digit one-dimension barcode on the side and a laser-etched DATAMATRIX two-dimension code at the bottom, which were used as the container of the saliva sample. A saliva collection support funnel (Nest) or saliva collection aid (Salimetrics) was used in tandem with the sample storage tube. In some embodiments, the storage tube includes FluidX Tri-Coded Next Gen Jack 1.9 ml sample storage tubes offered by Brooks Life Sciences and/or 0.5 ml Tri-coded tubes offered by Azenta Life Sciences.

Saliva Sample Receiving and Accessioning in Lab:

Samples were transported to the lab, removed from bags and visually examined for any leakage or damage. Samples that pass the pre-screening step were moved to the lab. The barcodes on the storage tubes were screened via a laboratory information management system (LIMS). Tubes with complete patient information in the LIMS and have no leakage (i.e., qualified samples), were placed in a bar-coded 48-format rack.

Saliva Reaction Buffer:

As part of sample preparation, the saliva sample was mixed with a unique buffer composition prepared specifically for saliva (referred to herein as Saliva Preparation Buffer). Preparation of the Saliva Preparation Buffer includes use of at least the following equipment: Biosafety cabinet or laminar flow hood (workspace capable of maintaining an aseptic environment); individual, sterile wrapped pipettes, pipette tips, such as 10 and 25 mL; pipette aid; pipettor, 1 mL or 200 μL and corresponding tips; and 50 ml sterile, nuclease-free Falcon tubes.

An exemplary Saliva Preparation Buffer comprises the following reagents/components:

0.5 M Bond-Breaker TCEP solution, (Tris(2-carboxyethyl)phosphine hydrochloride, neutral pH), Sterile, DNase-, Rnase- and Protease-Free grade, ThermoFisher Scientific, catalog number 77720, 5 mL;

RNase inhibitor, human placenta, 40,000 units/ml, Sterile, Dnase-, Rnase-Free grade, New England Biolabs, catalog number M0307L, 10,000 units, 250 ul/tube;

Amphotericin B solution, 250 μg/ml in deionized water, sterile, Sigma-Aldrich, catalog number A2942, 100 ml (or similar antifungal at an appropriate concentration to prevent fungal contamination and growth);

Penicillin-Streptomycin Solution, 100×, a mix of Penicillin (10,000 IU) and Streptomycin (10,000 μg/ml) in a 100-fold working concentration, Sterile, Corning, catalog number 30-002-CI (or similar antibiotics at an appropriate concentration to prevent bacteria contamination and growth;

Nuclease-free water, Sterile, Millipore/Sigma, W4502, Dnase-, Rnase- and Protease-Free grade; and Disinfectant, such as 70% ethanol.

Preparation of the ingredients includes at least the following steps: clean work surface with appropriate disinfectant; disinfect reagent bottles prior to placing on work surface; aliquot nuclease-free water, 40 mL in 50 mL sterile Falcon tube, store at room temperature (RT); aliquot Amphotericin B 4 ml/tube (in 5 ml sterile corning tube), store at −20° C.; aliquot Penicillin/Streptomycin, 1 ml/tube (in sterile Eppendorf tubes), store at −20° C.

Preparation of the Saliva Preparation Buffer includes at least the following steps:

1. Clean work surface with appropriate disinfectant;
2. Disinfect reagent bottles (aliquot, except RNase inhibitor) prior to placing on work surface;
3. For example, to prepare 5 mL buffer (for 1000 tests):
   3.1. in a 15 mL sterile falcon tube, add 4.3 mL nuclease-free water;
   3.2. add 400 uL TCEP;

3.3. using a sterile pipette, add 50 ul of RNase inhibitor;

3.4 thaw a tube of Amphotericin and a tube of Penicillin/Streptomycin, using a sterile pipette, aseptically add 200 uL of Amphotericin and 50 uL of Penicillin/Streptomycin to the 15 mL falcon tube;

4. Record lot information and preparation in a laboratory-controlled notebook;

5. Assign laboratory appropriate identification (e.g. lot number);

6. Cap the tube securely and mix thoroughly by inverting the tube;

7. Withdraw 100 ul of medium for QC sample;

8. Label the bottle as:

Saliva Reaction BUFFER

Lab ID: (Insert laboratory appropriate identification, such as STB1 as Summit Buffer 1)

DOM: (Insert current date of manufacture)

Expires: (Insert date 1 month after manufacture date)

Store at 2-8° C.

9. Store at 2-8° C., add 5 ul/each test together with 30 uL saliva and 5 uL proteinase K when performing SalivaFAST testing; and 10. Perform sterility check.

Another exemplary Saliva Preparation Buffer essentially comprises at least the following reagents/components/solutions:

A 40 µM TCEP solution (0.5 M Bond-Breaker TCEP solution, (Tris(2-carboxyethyl)phosphine hydrochloride, neutral pH), Sterile, DNase-, RNase- and Protease-Free grade, ThermoFisher Scientific, catalog number 77720, 5 mL), which consists of a ratio of water to TCEP of 11.5 to 1, respectively (e.g., 46 mL of water and 4 mL of TECP);

A TP-RAP solution (the TCEP solution above, plus additional components), which includes the 40 µM TCEP solution (approximately 949 µL), an RNase inhibitor (approximately 1 µL), a Penicillin-Streptomycin solution (approximately 10 µL), and an Amphotericin B solution (approximately 40 µL); and A saliva protease buffer solution (TP-RAP solution above, plus a protease (e.g., Proteinase K), which includes the TP-RAP solution and Proteinase K in a 1:1 ration (approximately 5 mL of each).

Preparation of the ingredients noted above includes at least the following steps (in a manner as previously described herein):

1. Prepare ~40 µM TCEP from 0.5 M stock solution;
2. Add 4 mL of 0.5 M TCEP to 46 mL of nuclease free water;
3. First add 4,745 µL of ~40 µM TCEP to a 10 mL tube;
4. Add 200 µL of Diluted Amphotercin-B solution;
5. Add 50 µL of Diluted Pennicilin streptomycin solution;
6. Add 5 uL of NEB Human Placenta Derived RNAse Inhibitor;
7. Add 5,000 uL (5 mL) of Promega Protinase K solution; and
8. Mix, label date, name, and expiration and store at 4° C. for up to one month.

Saliva Sample Preparation:

Each well for analysis contained 10 µL/well of a Sample Prep Mix (SPM). The SPM contains the Saliva Preparation Buffer and a protease (Proteinase K). In particular, the 96-well SPP contained 10 µL SPM (5 µL Saliva Preparation Buffer and 5 µL Proteinase K (Promega))/well, dispensed into each well using a multichannel equalizer or Viaflow (Integra). Samples were decapped with a semi-automated 6-channel decapper (Brooks) or Hamilton I.D. Capper inside the biosafety cabinets. Caps were temporarily placed on the cap carrier rack when using the 6-channel decapper. Approximately 30 µL of saliva were transferred from the tubes in the 48-well rack using the E1-ClipTip electronic multichannel (8-channels) equalizer to the 96-well SPP containing the 10 µL SPM and pipetting well. Two 48-well racks of samples will fill one 96-well SPP. Samples were recapped (6 at a time if using the 6-channel decapper or 48 at a time if using the automated 48-format decapper). The saliva and SPM were mixed well by placing the plates on the digital microplate shaker @ 500 RPM for 1 minute. The plate was placed on the miniAmp 96-well PCR instrument at 95° C. for 5 minutes, and 4° C. on hold. The entire racks of samples were then brought to the temporary sample storage area. Any of the samples that require repeat testing were identified from the temporary sample storage area. Repeat testing is only allowed one time.

PCR Reagent Preparation and Plate Setup (Saliva Testing):

A plate containing a PCR master mix (herein referred to as a PCR Master Mix Plate (PMMP)) was used and included 12.5 µL of PCR master mix dispensed into each well of the plate using a multichannel equalizer or Viaflow (Integra) on to a 96- or 384-well plate. The PCR master mix was composed of 10 µL Luna Universal Probe One-Step Reaction Mix, 1 µL Luna Warmstart RT enzyme Mix, and 1.5 µL of N1/RNP primer/probe. The 1.5 µL N1/RNP primer/probe was made as: 6.7 µM working stocks of the N1 and RNP primers and 1.7 µM FAM-labeled N1 and ATTO-64 µM labeled RNP probe by adding 50.25 µL of each 100 µM primers and probe stock to 524 µL IDTE buffer (pH7.5).

A 96- or a 384-well PMMP was placed into a PCR workstation and 7.5 µL of treated saliva sample from the Saliva Sample Preparation Step was added to each designated well of the PMMP. The treated saliva sample was then mixed with the PCR master mix by pipetting. Then, 7.5 µL of positive control (IDT synthetic 2019-SARS-CoV-N control, 4000 copies/uL), and negative control (IDT Hs-RPP30 control, 4000 copies/µL) for SARS-CoV-2, and no-template control (NTC-water) were added to designated PCR wells for the controls (1 positive control, 1 negative control, and NTC per plate) and mixes by pipetting, avoiding introducing bubbles.

PCR Thermal Profile (Amplification Area) (Saliva Testing):

Load the plate into a Bio-Rad CFX or a QuantStudio PCR machine, Open master file "ST-COV-PCR protocol", and run the following thermocycler conditions:

1. Step 1: 55° C. 10 minutes, 1 cycle;
2. Step 2: 95° C. 1 minute, 1 cycle; and

Step 3: 95° C. 10 sec, 60° C. 30 sec (+plate read at both FAM channel for N1 target & Cy5 channel for RNP target) for 40 cycles.

Data Interpretation (BioRad CFX Opus 96-Well Format) (Saliva Testing):

The Bio-Rad CFX reports Cq values, in which the Cq value files (csv file) are exported from the PCR machine to the OvDx LIMS. Interpretation of the Cq values (DETECTED, NOT DETECTED, and INVALID) will be exported to the OvDx LIMS according to the following criteria:

| | Cq: N1 (FAM channel) | Cq: RNP (Cy5 channel) |
|---|---|---|
| (COVID-19 positive) DETECTED | ≤36 | Any number or NaN |

| | Cq: N1 (FAM channel) | Cq: RNP (Cy5 channel) |
|---|---|---|
| (COVID-19 negative) NOT DETECTED | >36 | ≤35 |
| INVALID | >36 | >35 |

If N1 is detected, the result is valid ad returns a "DETECTED" regardless of value for RNP. If N1 is NOT detected and RNP is ≤35, then return a result of "NOT DETECTED". If RNP Cq value >35 and if N1>36, then the sample is requeue for retesting. After retesting, if the RNP is still >35, then the provider must be contacted to collect another sample. NaN=not a number.

Nasal Swab (Anterior Nares) Sample Collection:

Nasal swab collection devices include, for example, a 1.9 ml storage tube (as previously described herein with regard to the saliva sample collection). The storage tube is filled with 1 ml a unique buffer composition specific to nasal swab samples (hereinafter referred to as Swab Transport Buffer), which will be used as the container of the nasal swab sample; and an oral/Nares swab by Nest will be used to swab the patient's anterior nares and later be placed inside the sample storage tube filled with the Swab Transport Buffer.

Swab Preparation Buffer:

As part of sample preparation, the swab sample was mixed with a unique buffer composition prepared specifically for swab samples (referred to herein as Swab Preparation Buffer). Preparation of the Swab Preparation Buffer includes use of at least the following equipment: Biosafety cabinet or laminar flow hood (workspace capable of maintaining an aseptic environment); individual, sterile wrapped pipettes, pipette tips, such as 10 and 25 mL; pipette aid; pipettor, 1 mL or 200 µL and corresponding tips; 50 ml sterile, nuclease-free Falcon tubes; Eppendorf repeater (50 mL capacity); 1.9 ml storage tubes; tube racks; and external thread cap tube decapper equipment (such as the LabElite I.D. Capper offered by Hamilton Storage).

The preparation of the Swab Transport Buffer further includes use of at least the following reagents/components:
- 10×TBE Buffer (Tris-Borate-EDTA, pH 8.2-8.4), Sterile, DNase-, RNase- and Protease-Free grade, Fisher BioReagents, catalog number BP133320, 20L;
- RNase inhibitor, human placenta, 40,000 units/ml, Sterile, DNase-, RNase-Free grade, New England Biolabs, catalog number M0307L, 10,000 units, 250 ul/tube;
- Amphotericin B solution, 250 µg/ml in deionized water, sterile, Sigma-Aldrich, catalog number A2942, 100 ml (or similar antifungal at an appropriate concentration to prevent fungal contamination and growth);
- Penicillin-Streptomycin Solution, 100×, a mix of Penicillin (10,000 IU) and Streptomycin (10,000 µg/ml) in a 100-fold working concentration, Sterile, Corning, catalog number 30-002-CI (or similar antibiotics at an appropriate concentration to prevent bacteria contamination and growth;
- Nuclease-free water, Sterile, Millipore/Sigma, W4502, DNase-, RNase- and Protease-Free grade; and
- Disinfectant, such as 70% ethanol.

Preparation of the ingredients includes at least the following steps: clean work surface with appropriate disinfectant; disinfect reagent bottles prior to placing on work surface; take the 1 L nuclease-free water in Sigma Sterile bottle and use it as container, removing 105.05 ml of water and allocating to three 50 mL falcon tubes (each falcon tube to have 34.5 ml of water); aliquot 10×TBE Buffer, 500 ml/bottle in Corning 500 ml sterile bottle, store at RT; aliquot nuclease-free water, 894.95 ml/bottle in Corning 1L sterile bottle, store at RT; aliquot Amphotericin B solution 4.4 ml/tube (in 5 ml sterile Corning tube), store at −20° C.; and aliquot Penicillin/Streptomycin, 1.1 ml/tube (in sterile Eppendorf tubes), store at −20° C.

Preparation of the Swab Preparation Buffer includes at least the following steps:
1. Clean work surface with appropriate disinfectant;
2. Disinfect reagent bottles (aliquot, except RNase inhibitor) prior to placing on work surface;
3. For example, to prepare 1.1L viral transport buffer:
   3.1. bring 1 bottle of nuclease-free water (894.95 ml/bottle);
   3.2. using a sterile 50 ml falcon tube, add 100 ml of 10×TBE Buffer;
   3.3. using a sterile pipette, add 55 µl of RNase inhibitor; and
   3.4 thaw a tube of Amphotericin B solution and a tube of Penicillin/Streptomycin, using a sterile pipette, aseptically add 4.4 ml of Amphotericin and 1.1 ml of Penicillin/Streptomycin to the bottle.
4. Record lot information and preparation in a laboratory-controlled notebook;
5. Assign laboratory appropriate identification (e.g. lot number);
6. Cap the tube securely and mix thoroughly by inverting the tube;
7. Withdraw 100 ul of medium for QC sample;
8. Label the bottle as:
SWAB TRANSPORT BUFFER
Lab ID: (Insert laboratory appropriate identification, such as STB2 as Summit Buffer 2)
DOM: (Insert current date of manufacture)
Expires: (Insert date 1 month after manufacture date)
Store at 2-8° C.
9. Store at 2-8° C., until dispensed into aliquots;
10. Aliquot 1 mL of prepared Swab Preparation Buffer into individual sterile 1.9 ml screw-capped tubes (Azenta) using Eppendorf repeater (50 mL capacity) and Brooks decapper;
11. Perform sterility check; and
12. Store tubes and any buffer remaining in the bottle at 2-8° C.

Swab Sample Preparation:

Each well for analysis contains 5 µL of Proteinase K (Promega))/well, dispensed into each well using a multi-channel equalizer or Viaflow (Integra). Samples were decapped with, for example, a semi-automated 6-channel decapper (Brooks) or automated Hamilton I.D. Capper inside the biosafety cabinets. Caps were temporarily placed on the cap carrier rack when using the 6-channel decapper. Approximately 35 µL of swab sample were transferred from the tubes in the 48-well rack using the E1-ClipTip electronic multichannel (8-channels) equalizer to the 96-well SPP containing the 5 µL of Proteinase K and pipetting well. Two 48-well racks of samples will fill one 96-well SPP. Samples were recapped (6 at a time if using the 6-channel decapper or 48 at a time if using the automated 48-format decapper). The swab samples and Proteinase K were mixed well by placing the plates on the digital microplate shaker @ 500 RPM for 1 minute. The plate is placed on the miniAmp 96-well PCR instrument at 95° C. for 5 minutes, and 4° C. on hold. The entire racks of samples were then brought to the temporary sample storage area.

PCR Reagent Preparation and Plate Setup (Swab Testing):

A plate containing a PCR master mix (herein referred to as a PCR Master Mix Plate (PMMP), includes 12.5 µL of PCR master mix dispensed into each well of the plate using a multichannel equalizer or Viaflow (Integra) on to a 96- or 384-well plate. The PCR master mix is composed of 10 µL Luna Universal Probe One-Step Reaction Mix, 1 µL Luna Warmstart RT enzyme Mix, and 1.5 µL of N1/RNP primer/probe. The 1.5 µL N1/RNP primer/probe will be made as: 6.7 µM working stocks of the N1 and RNP primers and 1.7 µM FAM-labeled N1 and ATTO-647 labeled RNP probe by adding 50.25 µL of each 100 µM primers and probe stock to 524 µL IDTE buffer (pH7.5).

A 96- or a 384-well PMMP was placed into a PCR workstation and add 7.5 µL of treated swab sample from the Swab Sample Preparation Step to each designated well of the PMMP. The treated swab sample is then mixed with the PCR master mix by pipetting, taking care to avoid introducing bubbles. The MLS then adds 7.5 µL of positive control (IDT synthetic 2019-SARS-CoV-N control, 4000 copies/uL), and negative control (IDT Hs-RPP30 control, 4000 copies/µL) for SARS-CoV-2, and no-template control (NTC-water) to designated PCR wells for the controls (1 positive control, 1 negative control, and NTC per plate) and mixes by pipetting, avoiding introducing bubbles. The MLS then places a transparent plastic qPCR film on the PMMP and seals the film with a plate sealer and spin briefly to remove bubbles with a plate spinner.

PCR Thermal Profile (Amplification Area) (Swab Testing):

Load the plate into a Bio-Rad CFX or a QuantStudio PCR machine, Open master file "ST-COV-PCR protocol", and run the following thermocycler conditions:

1. Step 1: 55° C. 10 minutes, 1 cycle;
2. Step 2: 95° C. 1 minute, 1 cycle; and

Step 3: 95° C. 10 sec, 60° C. 30 sec (+plate read at both FAM channel for N1 target & Cy5 channel for RNP target) for 40 cycles.

Data Interpretation (BioRad CFX Opus 96-Well Format) (Swab Testing):

The Bio-Rad CFX reports Cq values, in which the Cq value files (csv file) are exported from the PCR machine to the OvDx LIMS. Interpretation of the Cq values (DETECTED, NOT DETECTED, and INVALID) will be exported to the OvDx LIMS according to the following criteria:

|  | Cq: N1 (FAM channel) | Cq: RNP (Cy5 channel) |
| --- | --- | --- |
| (COVID-19 positive) DETECTED | ≤36 | Any number or NaN |
| (COVID-19 negative) NOT DETECTED | >36 | ≤35 |
| INVALID | >36 | >35 |

If N1 is detected, the result is valid ad returns a "DETECTED" regardless of value for RNP. If N1 is NOT detected and RNP is ≤35, then return a result of "NOT DETECTED". If RNP Cq value >35 and if N1>36, then the sample is requeue for retesting. After retesting, if the RNP is still >35, then the provider must be contacted to collect another sample. NaN=not a number.

Viral load monitoring by RT-qPCR testing of 231 matched specimens sets from COVID-19 patients was conducted by the inventors in a prospective longitudinal study. For the example below (Example 1), four specimen types were assessed: RNA extract from nasal swab (SwabCLEAR), RNA extract from saliva (SalivaCLEAR), saliva without extraction (SalivaFAST), and combined saliva and nasal swab without extraction (Spit-N-Swab). Nasal swab and saliva are comparable specimens for detection of SARS-CoV-2. Although viral load was generally higher in nasal swab compared to matched saliva, this difference diminished over the course of infection and had no impact on clinical sensitivity (see FIGS. 7, 9, and 12). Extraction-free testing of combined nasal swab and saliva resulted in slightly lower Cycle Threshold (Ct) values compared to extraction-free saliva testing (see FIG. 13), further supporting higher viral load in the nasal cavity compared to the oral cavity.

Although RNA extract from saliva demonstrated a slightly increased viral load compared to extraction-free saliva, there was excellent positive agreement between matched specimens (see FIG. 10). These findings suggest that RNA extraction is an expendable step for RT-qPCR testing for SARS-CoV-2, as others have observed. Extraction-free RT-qPCR represents a new clinical testing paradigm during the COVID-19 pandemic. Saliva is an emerging specimen type that has utility for other respiratory pathogens.

Example 1

The 2019-nCoV CDC real-time RT-qPCR assay was modified, targeting the nucleocapsid gene of SARS-CoV-2 (N1 and N2) and the human ribonuclease P (RNP) gene, for extraction-free testing of saliva. Assay performance was compared using RNA extract from nasal swab, RNA extract from saliva, unprocessed saliva, and unprocessed saliva combined with nasal swab at the time of collection—designated as SwabCLEAR™, SalivaCLEAR™, SalivaFAST™, and Spit-N-Swab™. The inventors focused on development of SalivaFAST for extraction-free saliva testing and further focused on validation of SalivaFAST.

Analytical validation was performed by spiking COVID-19-negative nasal swab and saliva specimens with varying concentrations of SARS-CoV-2 positive control material (2-100 genome equivalents per microliter, GE/µL). Assay precision at these low viral loads corresponded to N1 Ct values >30 with coefficients of variation spanning 1.02-4.26% for SwabCLEAR and 0.95-4.33% for SalivaFAST and, respectively (see FIG. 7A). Compared to SwabCLEAR, SalivaFAST generally had higher Ctvalues at low viral loads, suggesting signal enhancement from RNA extraction of nasal swabs or inhibition by saliva matrix. As expected RNP Ct values, which are based on an intrinsic host target, were more variable but unaffected by SARS-CoV-2 (see FIG. 9B). The SalivaFAST limit of detection (LoD) was determined to be 4 GE/µL (see FIG. 9C). Such data suggest that extraction-free saliva testing has acceptable analytical performance compared to RNA extract from nasal swab.

The pre-analytical phase from specimen collection to laboratory testing is complicated by variables related to specimens, transport, and environmental conditions. We assessed the stability of samples tested by SalivaFAST after 2 weeks. The amount of detectable SARS-CoV-2 RNA diminished, with a mean N1 Ct increase of 1.56 and 1.83 for specimens stored at 4° C. and −80° C., respectively (see FIGS. 7D and 7E) (n=8, p=0.004 and p=0.008).

Clinical Validation of RNA Extracts from Nasal Swab and Saliva Specimens

The performance of the 2019-nCoV CDC real-time RT-qPCR assay has been extensively studiedand validated using RNA extracts from nasal swabs. To begin clinical validation of SalivaFAST, we collected matched nasal swab and saliva specimens prospectively from 137 patients of which 19

Figure 8A:
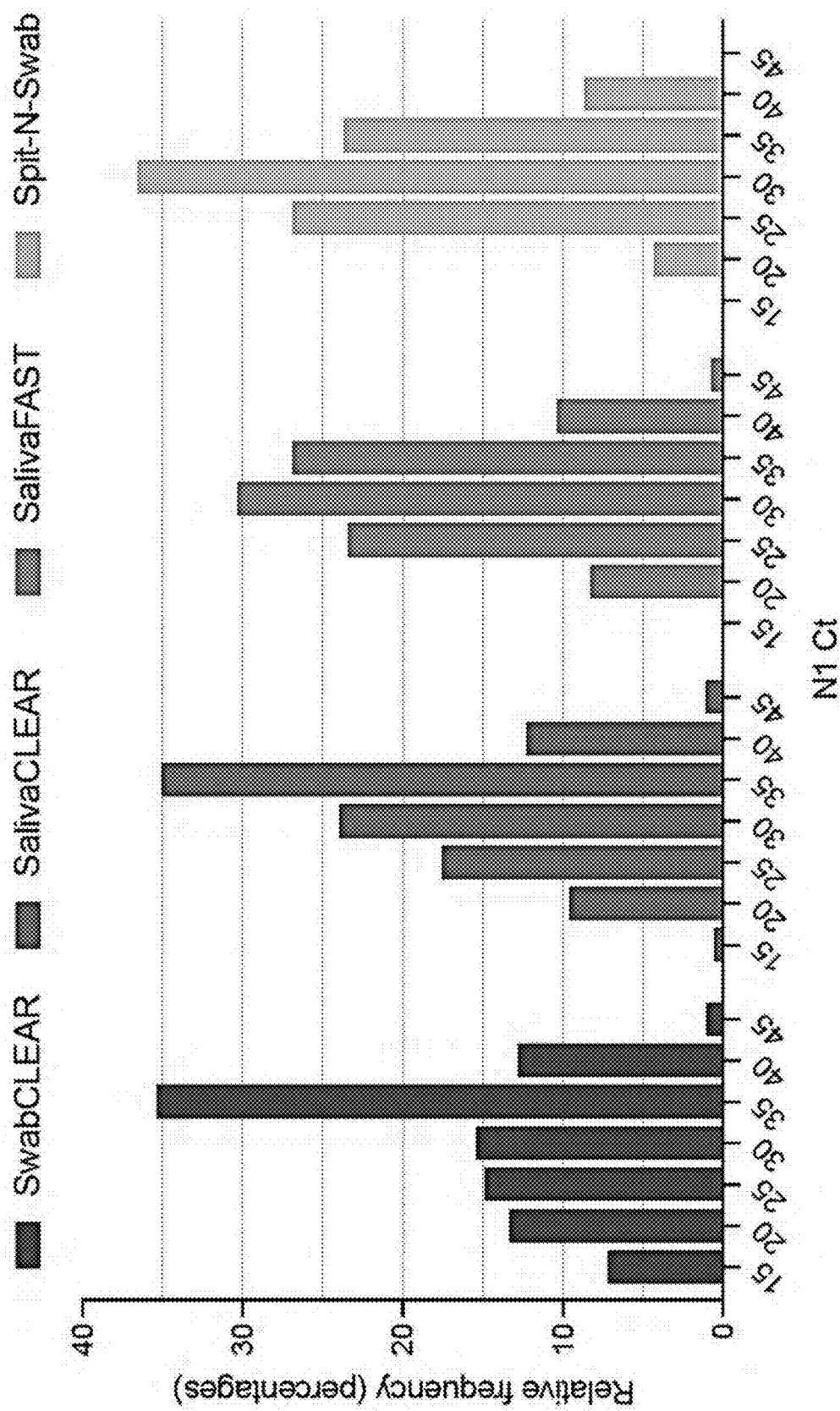
FIGS. 8A and 8B are graphs illustrating the distribution of cycle threshold (Ct) values from clinical samples having undergone testing in accordance with methods of the present invention. Matched RNA extracts from nasal swab samples (SwabCLEAR), RNA extracts from saliva samples (SalivaCLEAR), extraction-free saliva samples (SalivaFAST), and extraction-free saliva samples with a combined nasal swab specimen samples (Spit-N-Swab) demonstrate viral loads across abroad range according to the N1 cycle threshold (Ct) value, with an abundance of low viral load samples (FIG. 8AA). Violin plots demonstrate the distribution of Ct values for the N1, N2, and RNP targets from all 3 assays (FIG. 8B).
Figure 8B:
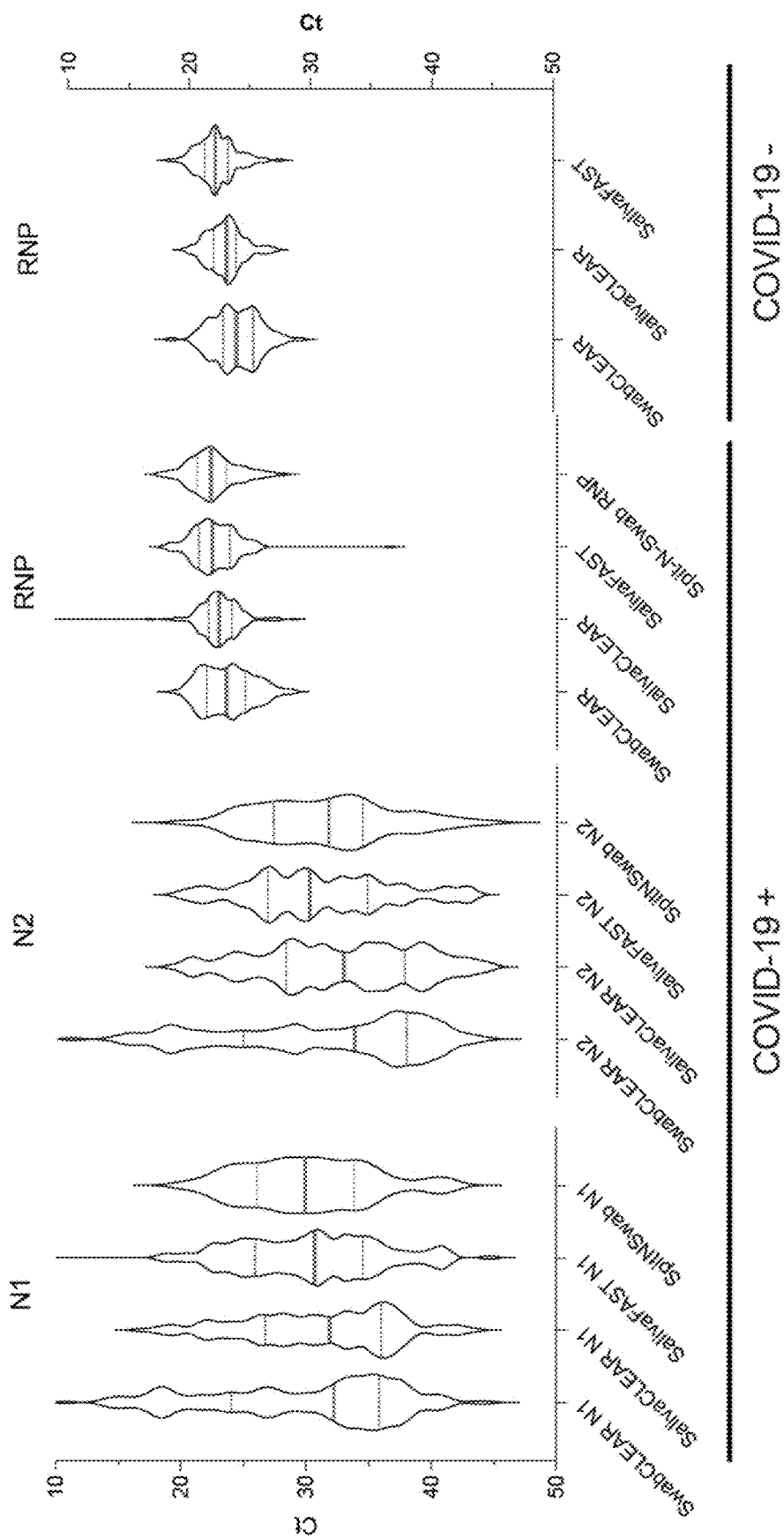
Figure 9A:
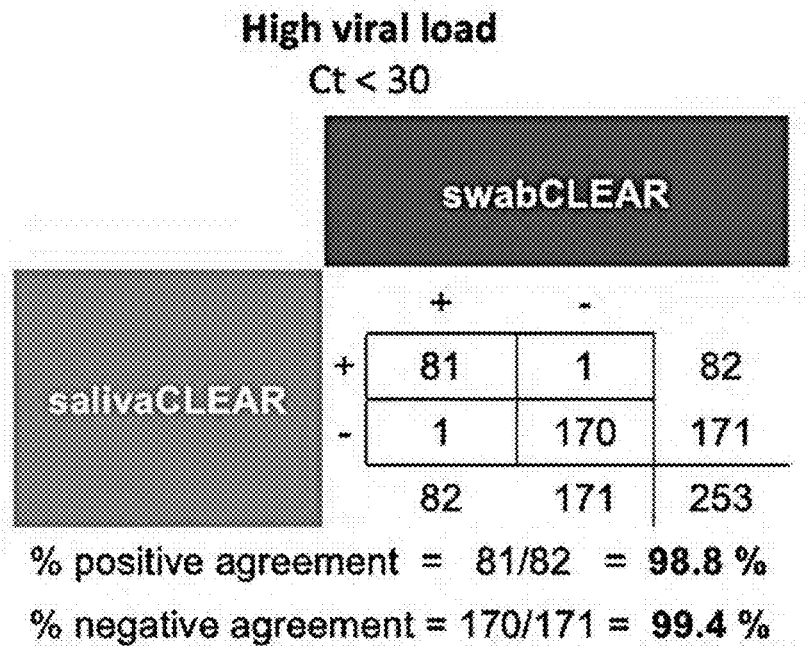
Figure 9B:
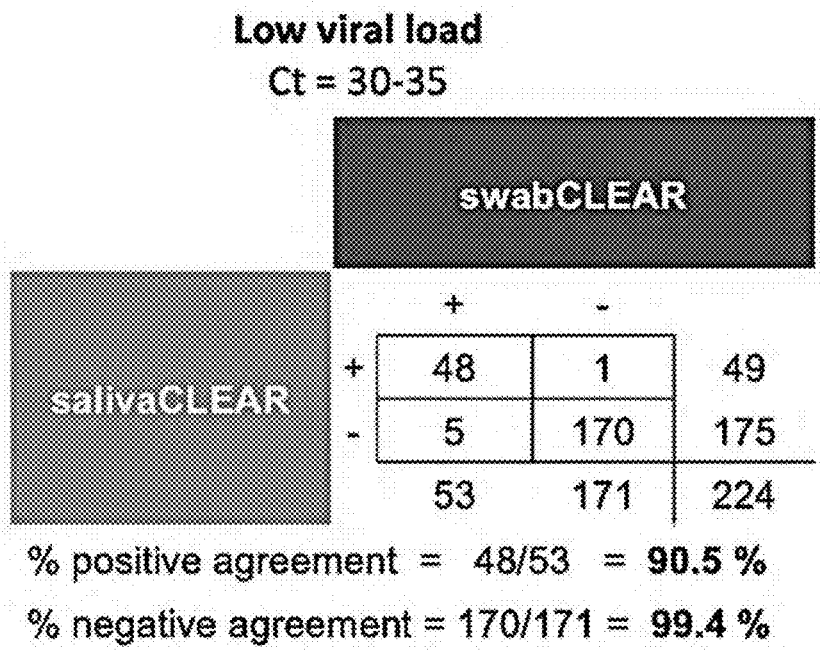
Figure 9F:
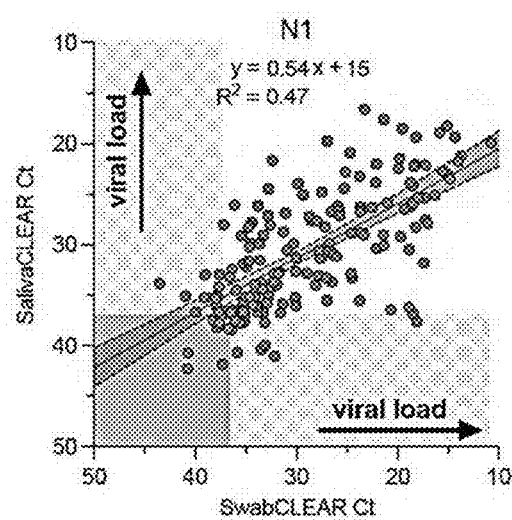
Figure 9G:
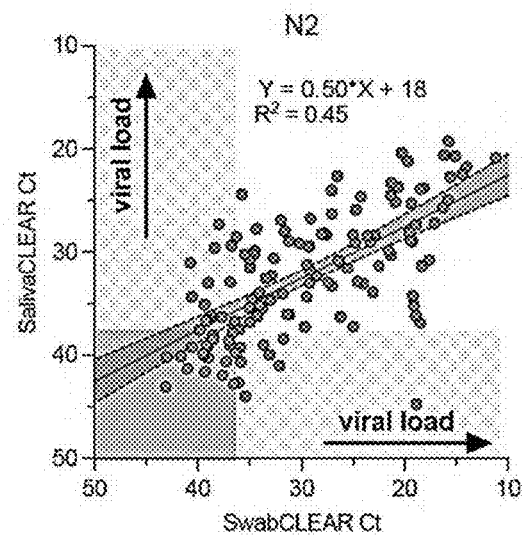
Figure 9H:
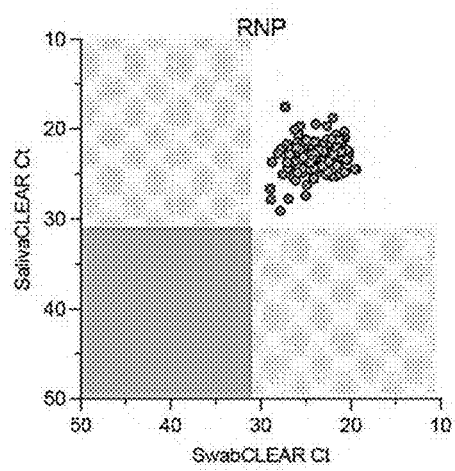

(13.9%) were diagnosed with COVID-19. COVID-19 patients underwent longitudinal testing until convalescence (see FIG. 15), yielding 231 matched sample sets. All specimen types demonstrated viral loads throughout the detectable range, including an abundance of low viral load specimens with N1 Ct values >30 (see FIGS. 8A and 8B). The RNP host gene signal was highly consistent across all specimen types regardless of COVID-19 status (see FIG. 8B).

To understand the impact of specimen type on SARS-CoV-2 RT-qPCR testing, N1 Ct values were compared between matched samples tested by SwabCLEAR and SalivaCLEAR, both of which depend on RNA extraction. Comparison of initial diagnostic samples revealed a mean Ct value increaseof 5.87 by SalivaCLEAR (n=19 sample pairs, p<0.001). By day 5 this difference decreased to 1.74 (n=16 sample pairs, p=0.034) (see FIGS. 9C and 9D). Throughout the disease course from diagnosis to convalescence, SwabCLEAR revealed a slightly higher viral load compared to SalivaCLEAR (29.71±0.30 versus 31.23±0.24, n=229 sample pairs, p<0.001, see FIG. 9E). Therefore, viral load by RT-qPCR is higher in the nasal cavity compared to the oral cavity and this difference diminishes over the course of infection.

A difference in viral load between specimen types has the potential to impact clinical sensitivity. Positive and negative agreement between SwabCLEAR and SalivaCLEAR specimens were assessed according to viral load. We defined high viral load as Ct<30, corresponding to >100 GE/µL (see FIG. 7A). High viral load was associated with 98.8% positive agreement. Low viral load specimens demonstrated 88.7% positive agreement (see FIGS. 9A and 9B). Negative agreement in matched specimens from patients withoutCOVID-19 was >99% at both levels. Moderate correlation was observed between N1 and N2 in each assay ($R^2$=0.45-0.47, see FIGS. 9F and 9G)) whereas the RNP Ct values were similar and consistent between specimens (see FIG. 9H, p=0.839). These data suggest that there is excellent diagnostic agreement betweenRNA extracts from paired nasal swab and saliva specimens for diagnosis of COVID-19 despite higher viral load of SARS-CoV-2 in the nasal cavity.

Clinical Validation of Extraction-Free Saliva Testing

Patients with COVID-19 symptoms, specifically for the alpha variant, or known close contacts of an infected individual were recruited to provide nasal swab and saliva specimens as part of an IRB-approved study. COVID-19 status was confirmed by an alternative method with FDA EUA. Nasal swab collection of anterior nares for testing was performed using the DNAGenotek ORE-100 device. Saliva collection was performed using either the DNAGenotek OM-505 device for or Falcon 50 mL conical tubes or cryotubes outfitted with a saliva collection aid (Salimetrics). Patients also provided a combined nasal swab and saliva specimen for a combined saliva and nares swab embodiment in which nasal swab was placed into saliva. Patients underwent longitudinal sample collection until viral clearance and/or withdrawal from the study (see FIG. 15). All samples were transported to the lab at ambient temperature within 72 hours and analyzed on the day of receipt in the laboratory.

Figure 10A:
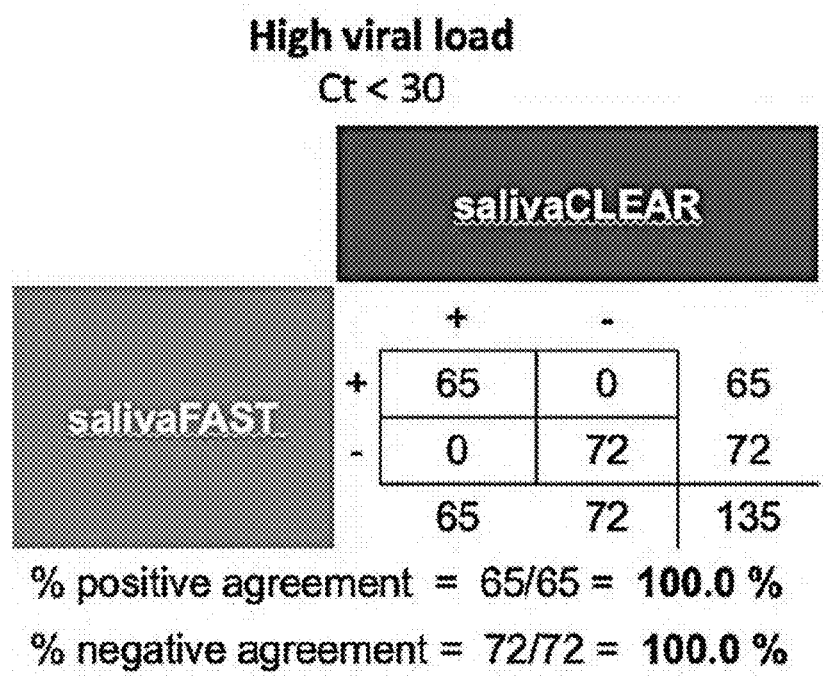
FIGS. 10A, 10B, 10C, 10D, 10E, and 10F are charts and graphs illustrating the impact of RNA extraction for RT-qPCR-based detection of SARS-CoV-2 in saliva. The positive and negative agreement between RNA extract from saliva samples (SalivaCLEAR) and extraction-free saliva samples (SalivaFAST) was assessed for high viral load nasal swab samples with a Ct<30 (FIG. 10A) and low viral loadnasal swab samples Ct=30-35 (FIG. 10B). Comparison of N1 Ct values from matched SalivaCLEAR and SalivaFAST samples demonstrated slightly lower viral load by SalivaFAST compared to SalivaCLEAR (FIG. 10C). There was moderate correlation between N1 Ct values (FIG. 10D) and N2 Ct values (FIG. 10E) for SalivaCLEAR and SalivaFAST. RNP values are relatively consistent for SalivaCLEAR and SalivaFAST (FIG. 10F).
Figure 10B:
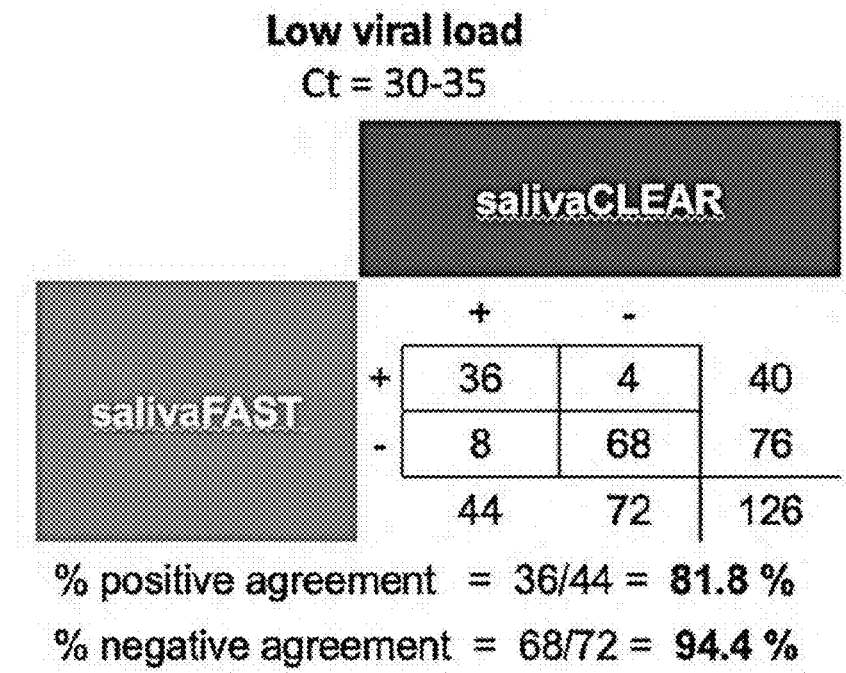
Figure 10C:
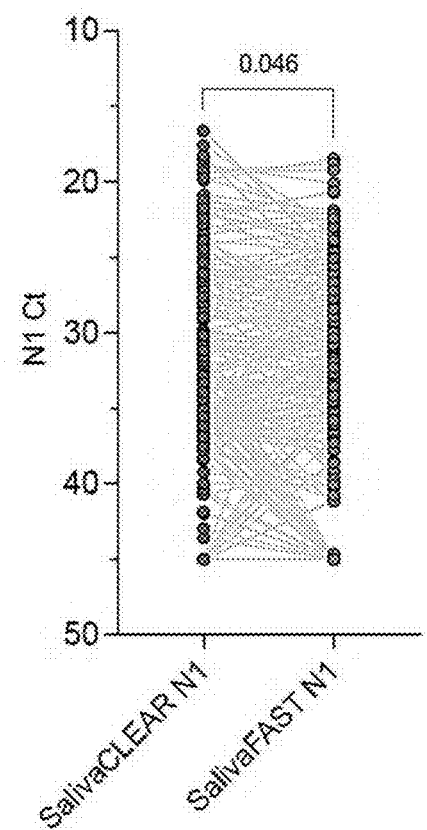
Figure 10D:
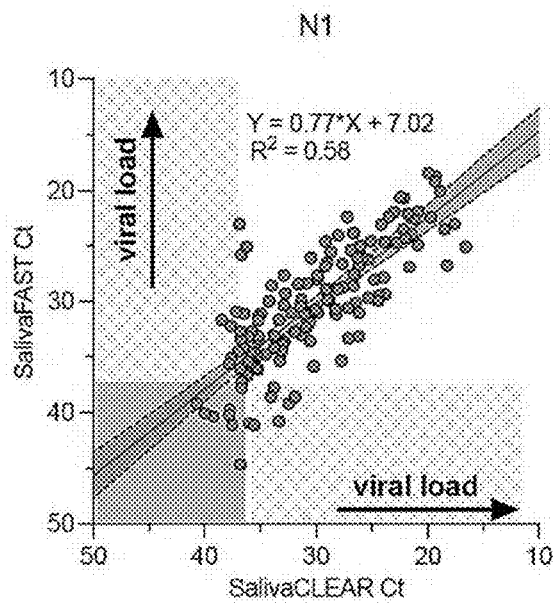
Figure 10E:
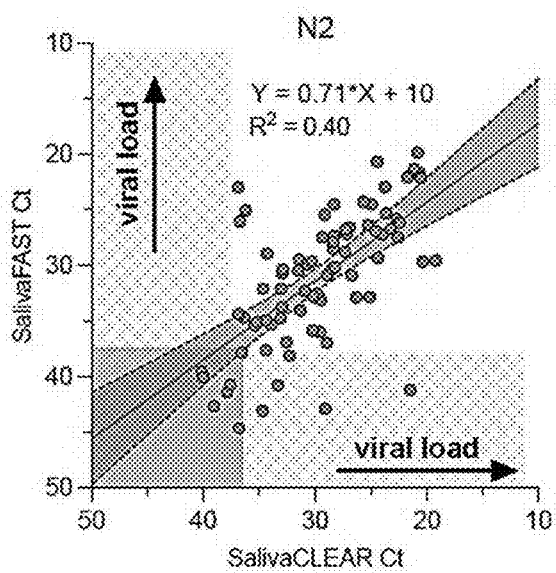
Figure 10F:
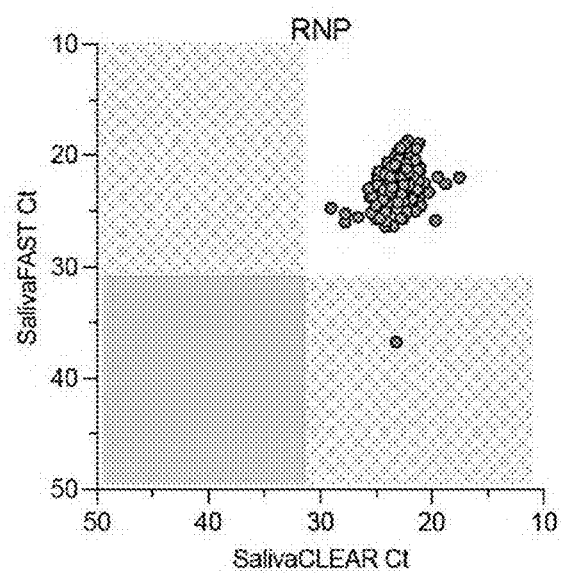
Figure 12D:
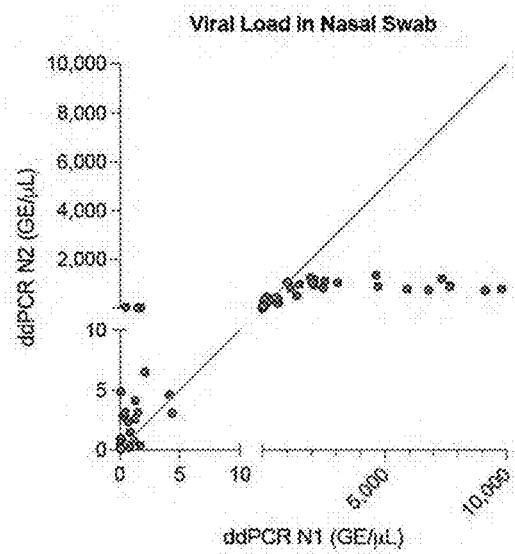
Figure 12E:
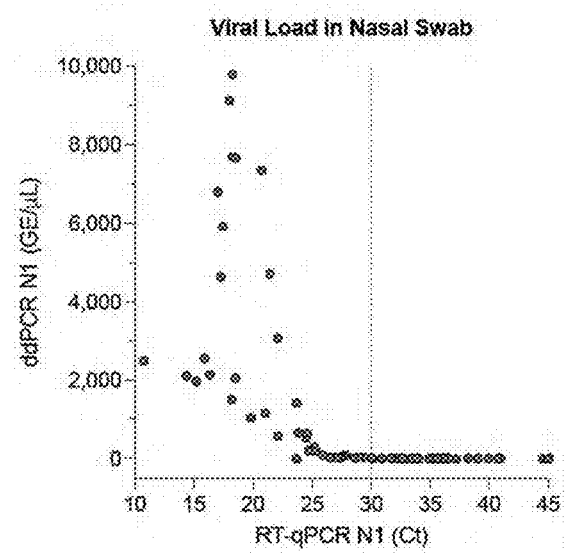
Figure 12F:
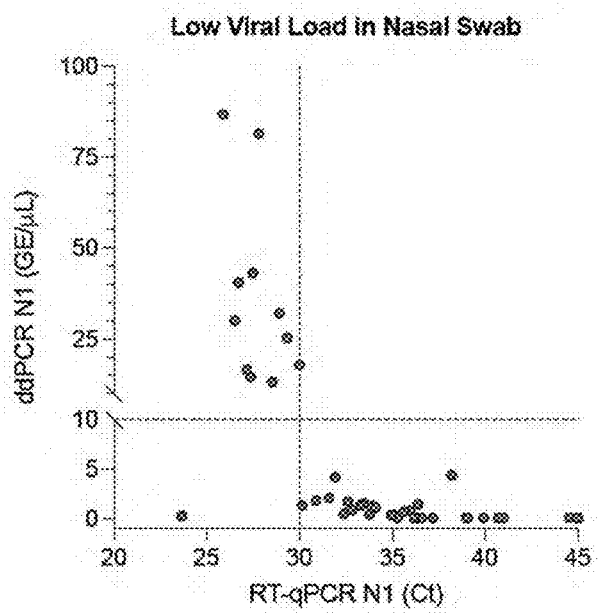
Figure 12G:
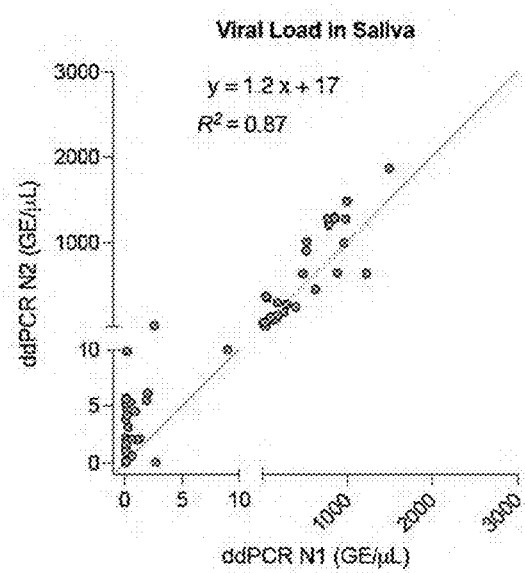
Figure 12H:
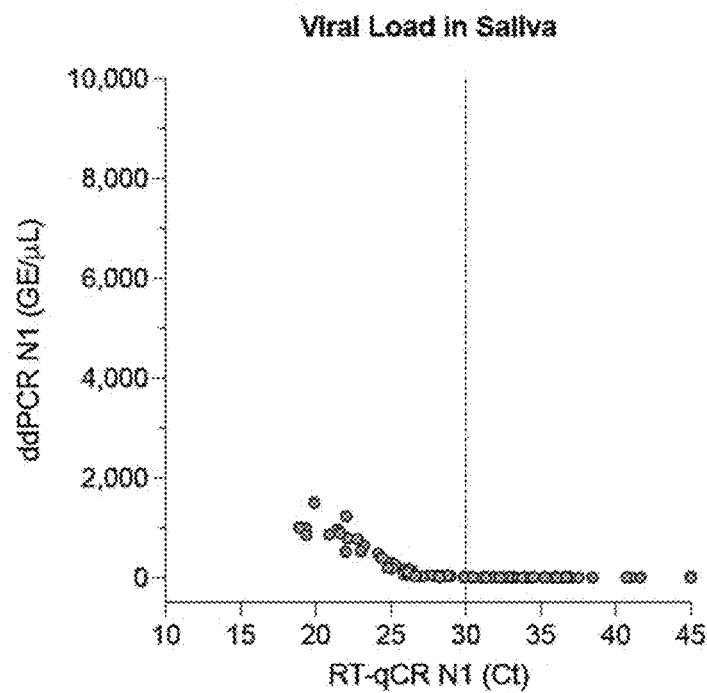
Figure 12I:
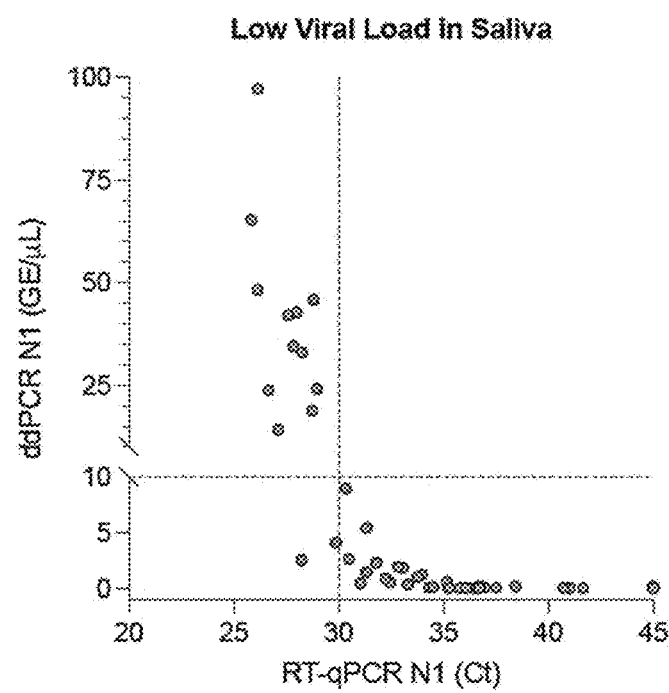
Figure 13A:
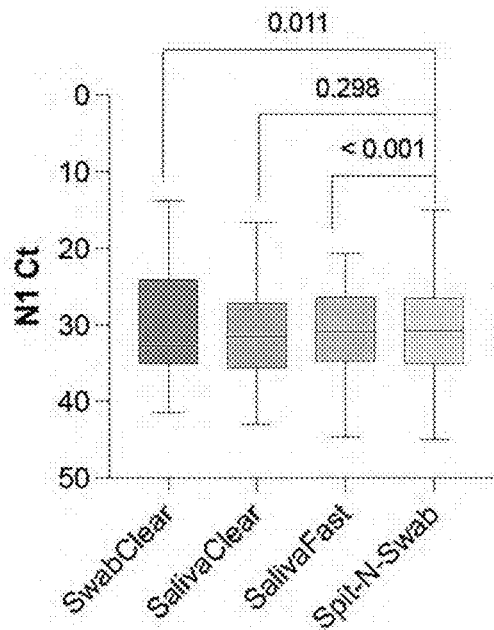
FIGS. 13A, 13B, 13C, and 13D are graphs illustrating extraction-free testing of saliva and combined nasal swab/saliva specimens. The N1 Ct values are compared across SwabCLEAR, SalivaCLEAR, SalivaFAST, and Spit-N-Swab (combined collection of nasal swab and saliva) (FIG. 13A). There was moderate correlation between SalivaFAST and Spit-N-Swab testing according to N1 (FIG. 13C) and the N2 (FIG. 13D) Ct values. The N1 Ct value of Spit-N-Swab specimens demonstrated low viral load samples missed by SalivaFAST (FIG. 13C). RNP Ct values were consistent in both assays (FIG. 13B).
Figure 13B:
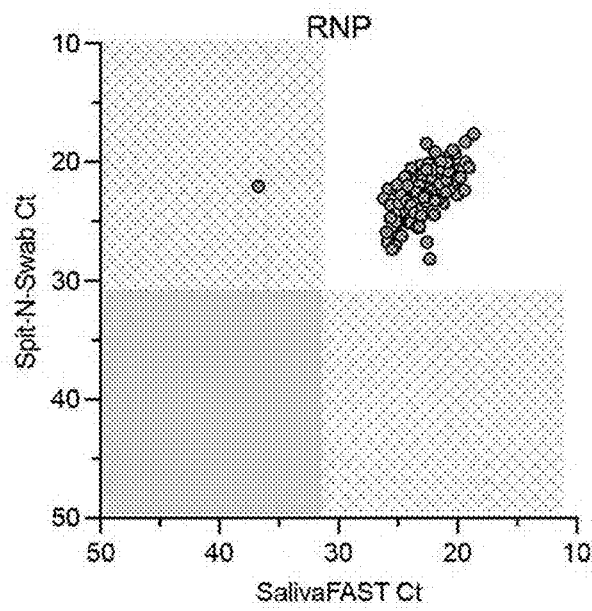
Figure 13C:
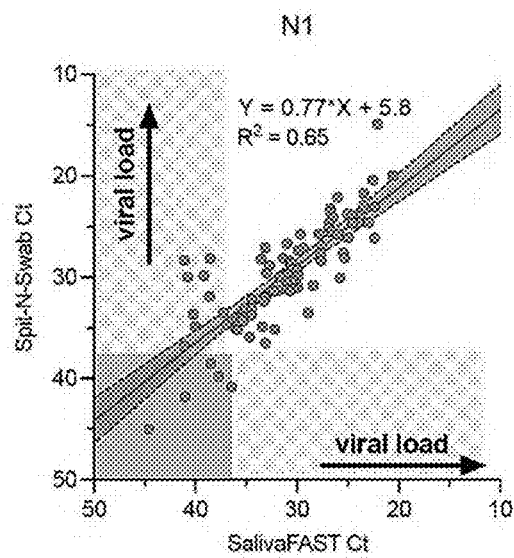
Figure 13D:
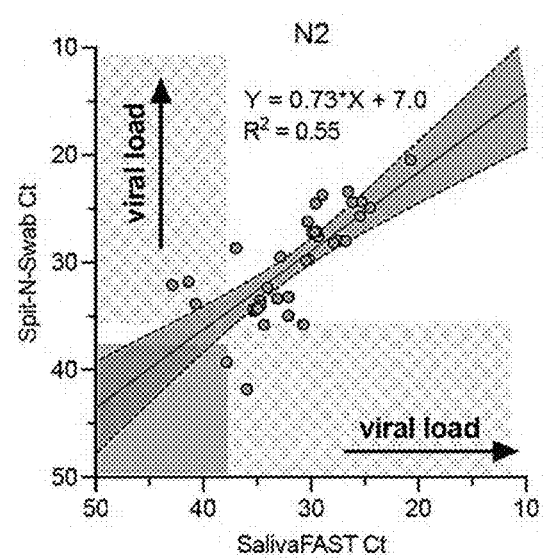

RNA extraction of saliva resulted in a significant but negligible increase in viral load, with a mean increased N1 Ct value of 0.07 for SalivaCLEAR compared to SalivaFAST (see FIG. 10C, n=202 sample pairs, p=0.046). Positive agreement between SalivaCLEAR and SalivaFAST varied according to viral load. Saliva specimens with high viral load (N1 Ct value ≤30) demonstrated 100.0% percent positive agreement between SalivaCLEAR and SalivaFAST (see FIG. 10A, n=65 sample pairs). Saliva specimens with low viral load (N1 Ct value 30-35) demonstrated 81.8% positive agreement (see FIG. 10B, n=44). Additionally, in some specimens with low viral load, SalivaCLEAR and SalivaFAST each detected SARS-CoV-2 not detected by the alternative method (see FIG. 10B), suggesting that RNA extraction represents a trade-off between RNA concentration and RNA yield. Comparison of N1 and N2 between assays again demonstrated moderate correlation (see FIGS. 9D and 9E, $R^2$=0.58 for N1, $R^2$=0.40 for N2). These data demonstrate that RNA extraction is not necessary for reliable COVID-19 diagnosis using saliva and that extraction-free testing does not compromise clinical sensitivity.

Comparison of Primer/Probe Sets

The 2019-nCoV CDC assay for detection of SARS-CoV-2 implements two primer/probe pairs targeting the nucleocapsid gene (N1 and N2). The CDC 2019 Novel Coronavirus (2019-nCoV) Real-Time RT-qPCR assay with primers and probes from Integrated DNA Technologies (IDT) was implemented. Briefly, this assay includes two primer/probes (N1 and N2) for detected of SARS-CoV-2 and one primer/probe for detection of ribonuclease P (RNP). For example, such primers/probes include: nCOV_N1 Forward Primer (catalog number 10006830); nCOV_N1 Reverse Primer (catalog number 10006831); nCOV_N1 Probe (catalog number 10006832); RNase P Forward Primer (catalog number 10006836); RNase P Reverse Primer (catalog number 10006837); and RNase P (ATTO™ 647) Probe (catalog number 10007062). The specific dilutions for preparing the final solution of primer/probe combinations include approximately 698 µL of IDTE (10 mM Tris, 0.1 mM EDTA), 67 µL of N1-F, 67 µL of N1-R, 17 µL of N1-probe, 67 µL of RNP-F, 67 µL of RNP-R, and 17 µL of RNP-probe.

RNA extraction of SwabCLEAR and SalivaCLEAR samples was performed using QIAamp Viral RNA mini Kit (Qiagen). Saliva samples collected in 50 mL falcon tubes or in a cryotube were tested directly by extraction-free SalivaFAST testing. 5 µL of swab RNA extract, 5 µL of saliva RNA extract, or 5 µL of raw saliva was added to PCR master mix to a volume of 20 µL into 96-well plates (Bio-Rad). RT-qPCR was performed by Bio-Rad CFX Connect Real-Time PCR Detection System with the CFX software. Cycle conditions were 55° C. for 10 mins; 95° C. for 1 min; and 95° C. for 10 seconds (s); and 60° C. for 30 s for 45 cycles. For analytical validation and assay controls, synthetic SARS-CoV-2 nucleic acid was used (Twist Biosciences).

Comparison of the performance of N1 and N2 within a single assay revealed a high degree of linearity for methods of the invention in which a nares swab was obtained ($R^2$=0.97), saliva ($R^2$=0.83), and extraction-free testing ($R^2$=0.82) (see FIGS. 11A-11C), suggesting that most COVID-19 cases were detected by both targets with similar assessment of viral load. Whereas N1 detected several low viral load COVID-19 cases missed by N2, especially in saliva, N2 offered no additional diagnostic value.

Quantitation of Viral Load by RT-qPCR and ddPCR

To evaluate the quantitative accuracy of viral load by RT-qPCR, ddPCR using the same primers and probes for N1 and N2 was also performed on RNA extracts from nasal swab and saliva specimens. First, a standard curve was generated for SalivaFAST First, quantitative accuracy and precision by ddPCR was performed. The recovered viral load in spiked samples following RNA extraction was 36.3-47.0% for nasal swab and 28.9-45.7% for saliva. Precision for N1 and N2 by ddPCR of extracts from nasal swab and saliva demonstrated a coefficient of variation (CV) of 5.6-12.3% and 4.5-19.1%, respectively (see FIG. 7A). Compare of viral loads in specimen pairs according to N1 and N2 generally demonstrated no correlation (see FIGS. 12B and 12C). In nasal swab specimens, N1 demonstrated a broad range of viral load whereas N2 in the same samples plateaued (see FIGS. 12D and 12E), again demonstrating inferior performance of N2. This pattern was not observed in saliva which was likely related to overall lower viral loads (FIG. 6G-H, $R^2=0.87$).

Comparison of Ct values by RT-qPCR with viral load by ddPCR revealed a logarithmic pattern with a clear inflection point for both nasal swab specimens (see FIGS. 6E and 6H). Ct values below this inflection point demonstrated linear agreement in both assays with better correlation for saliva compared to nasal swab specimens. Ct values above this inflection point corresponded to low viral load (<10 GE/μL) (see FIGS. 6F and 6I). Taken together, these data confirm that viral loads are higher in nasal swab samples and that Ct values no longer have quantitative value when greater than about 30.

A Combined Nasal Swab and Saliva Specimen is a Viable Specimen Type

Figure 7A:
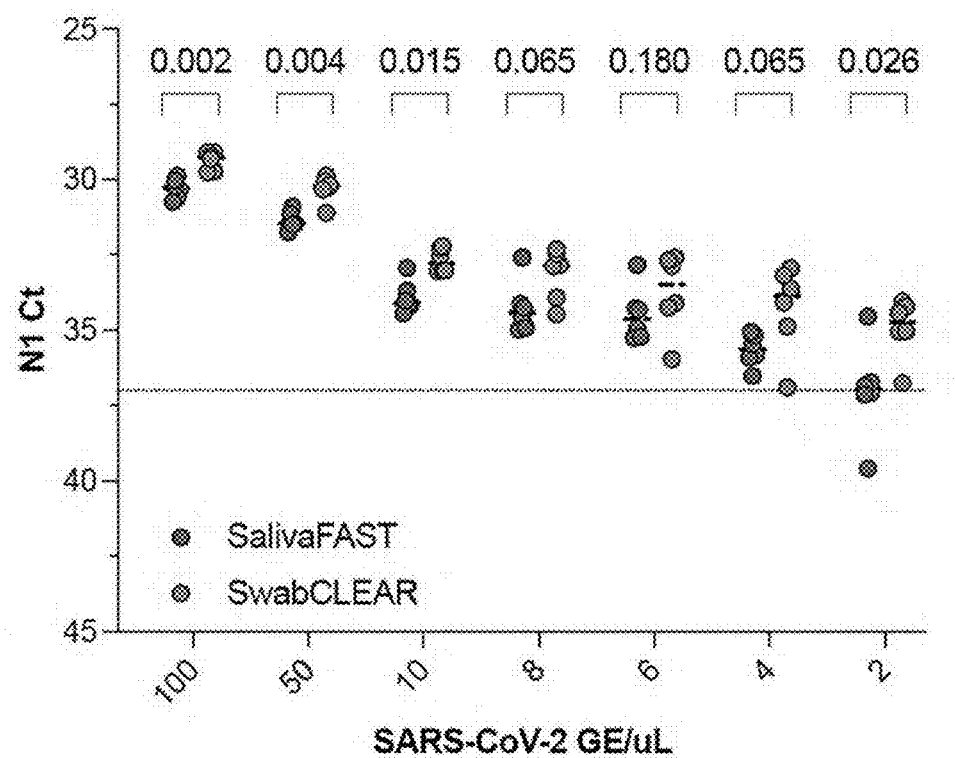
FIGS. 7A, 7B, 7C, 7D, and 7E are graphs illustrating analytical validation of extraction-free saliva testing in accordance with the methods of the present invention. RT-qPCR was performed on negative saliva (SalivaFAST) and nasal swabs (SwabCLEAR) samples that were piked with SARS-CoV-2 control material to demonstrate similar performance for N1 (FIG. 7A) and RNP (FIG. 7B). The limit of detection (LoD) of SalivaFAST was confirmed by analysis of 20 samples at 4 GE/μL on 3 separate thermocyclers (FIG. 7C). SalivaFAST was performed at 0 and 2 weeks, which demonstrated a slight decreased viral load at both 4° C.
Figure 7B:
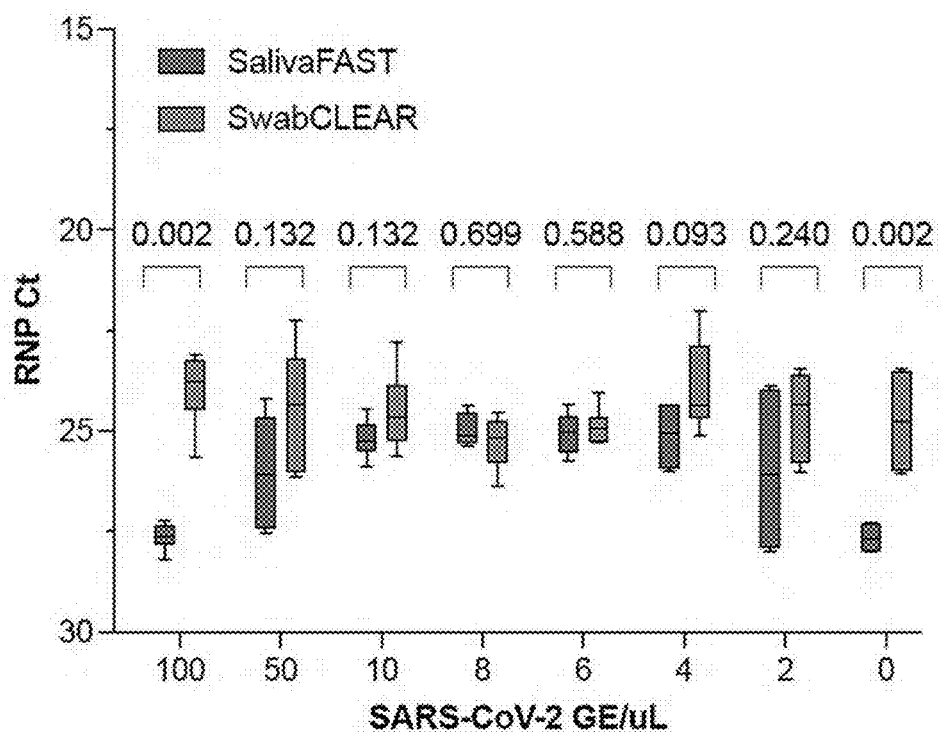
Figure 7C:
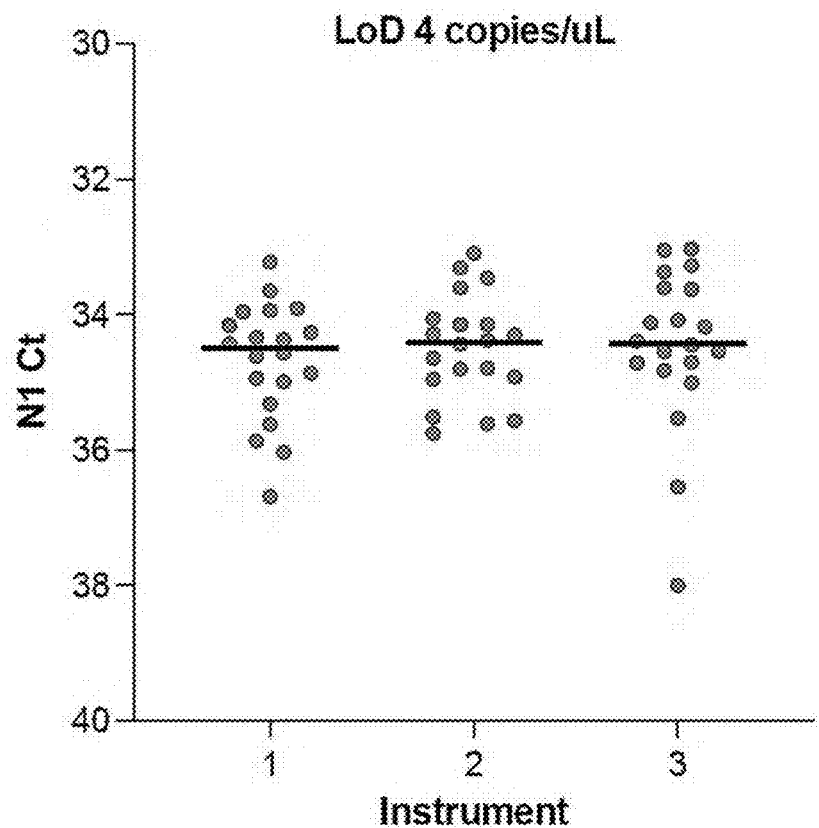
Figure 7D:
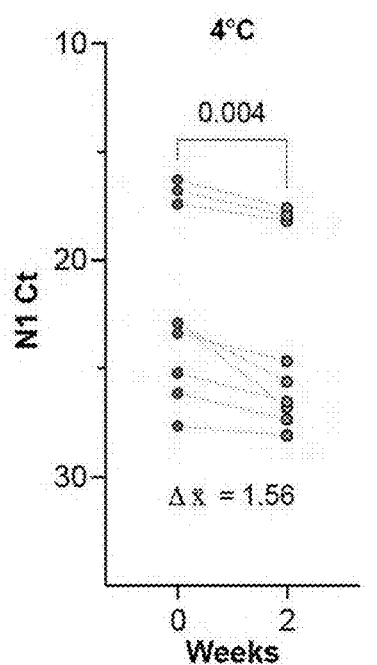
Figure 7E:
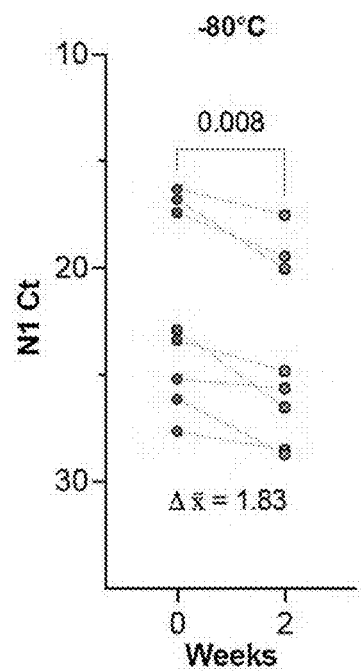

Extraction-free testing of combined nasal swab and saliva specimens (i.e., Spit-N-Swab) was evaluated for detection of SARS-CoV-2. COVID-19 patients provided saliva specimens in which nasal swabs were immersed. These specimens were tested directly without RNA extraction. Spit-N-Swab demonstrated a Ct increase of 1.6 compared to SwabCLEAR (n=104 specimen pairs, p=0.011) and a Ct decrease of 1.1 compared to SalivaFAST (n=90 specimen pairs, see FIG. 9A, p<0.001) (FIG. 7A). Spit-N-Swab may improve the clinical sensitivity of SalivaFAST, given that low viral load was detected in some Spit-N-Swab specimens with a negative matched SalivaFAST specimen (see FIG. 13C). These data suggest that a combined nasal swab and saliva specimen is viable for extraction-free testing and may enhance sensitivity in COVID-19 patients with low viral load infections.

Morning Versus Afternoon Collection

Figure 14A:
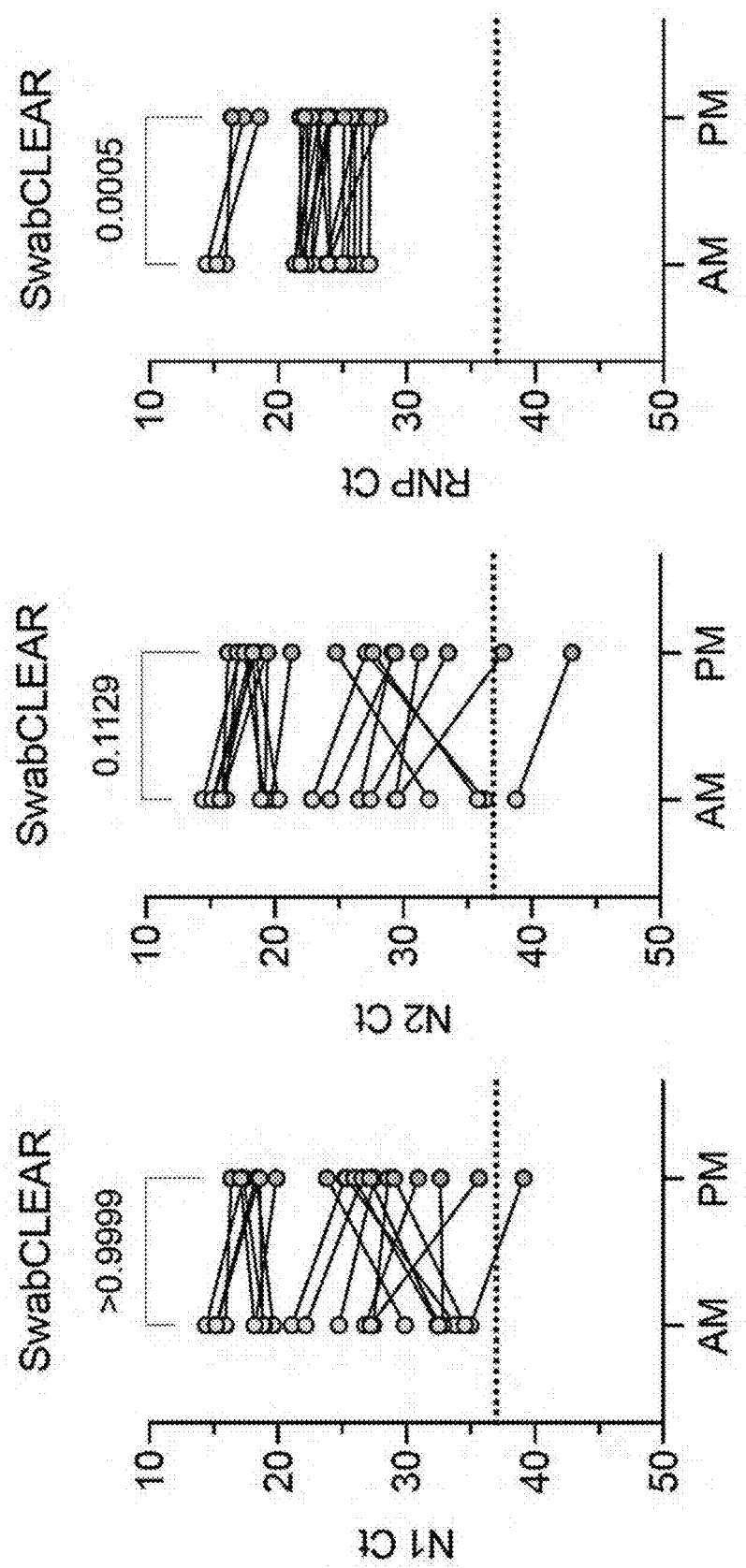
FIGS. 14A, 14B, and 14C are graphs illustrating the impact of morning versus afternoon collection. Morning (AM, yellow) and afternoon (PM, blue) samples are compared for SwabCLEAR (FIG. 14A), SalivaCLEAR (FIG. 14B), and SalivaFAST (FIG. 14C). RNP Ct values were slightly lower in the PM compared to the AM for SwabCLEAR (FIG. 14A, right panel) and SalivaCLEAR (FIG. 14B, right panel). SalivaFAST demonstrated a similar trend that was not significant (FIG. 14C, right panel). Whereas the N1 Ct values did not differ significantly between AM and PM for SwabCLEAR (FIG. 14A, left panel) and SalivaCLEAR (FIG. 14B, left panel), SalivaFAST demonstrated significantly increased N1 (FIG. 14C, leftpanel) and N2 (FIG. 14C, center panel) Ct values in the PM compared to the AM. Assay threshold for N1 and N2 targets are represented by horizontal dotted lines.
Figure 14B:
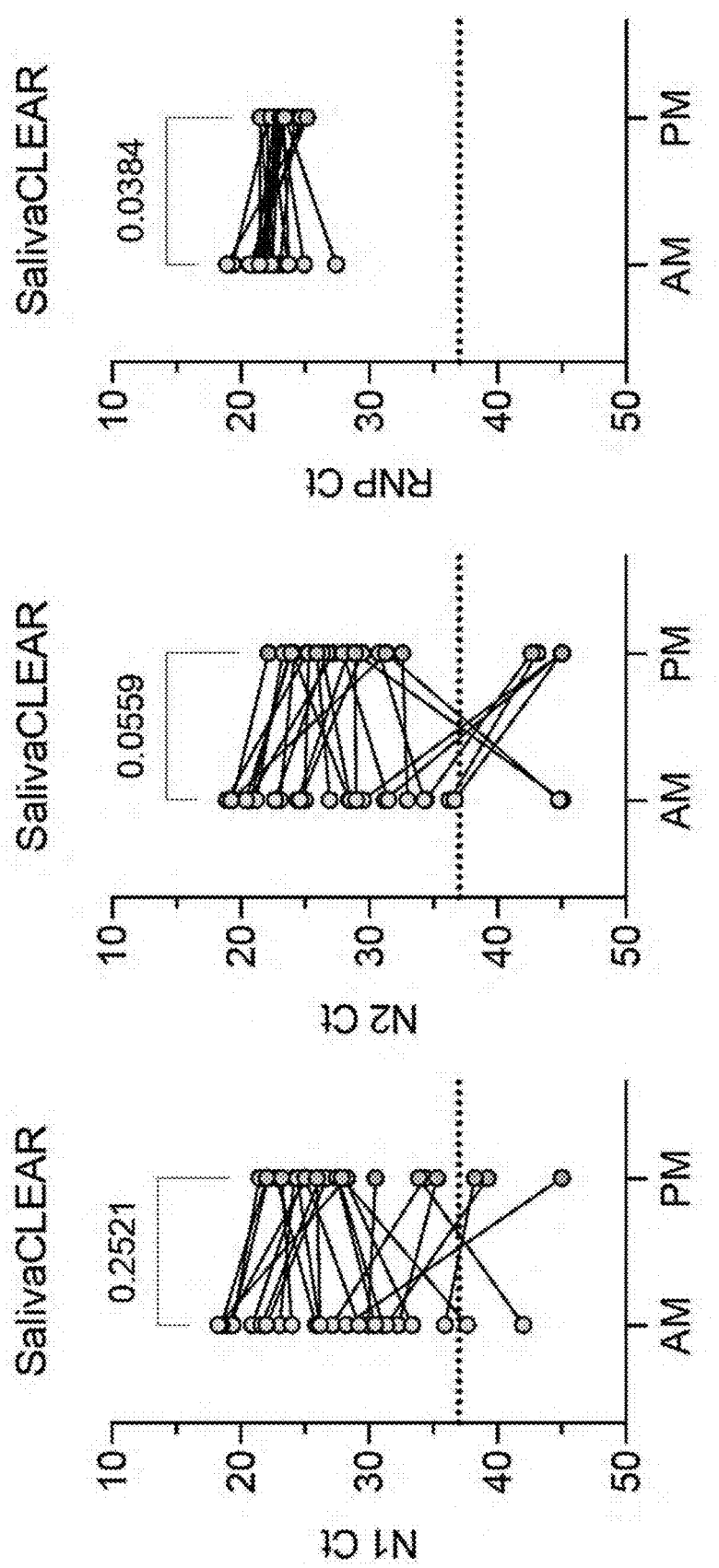
Figure 14C:
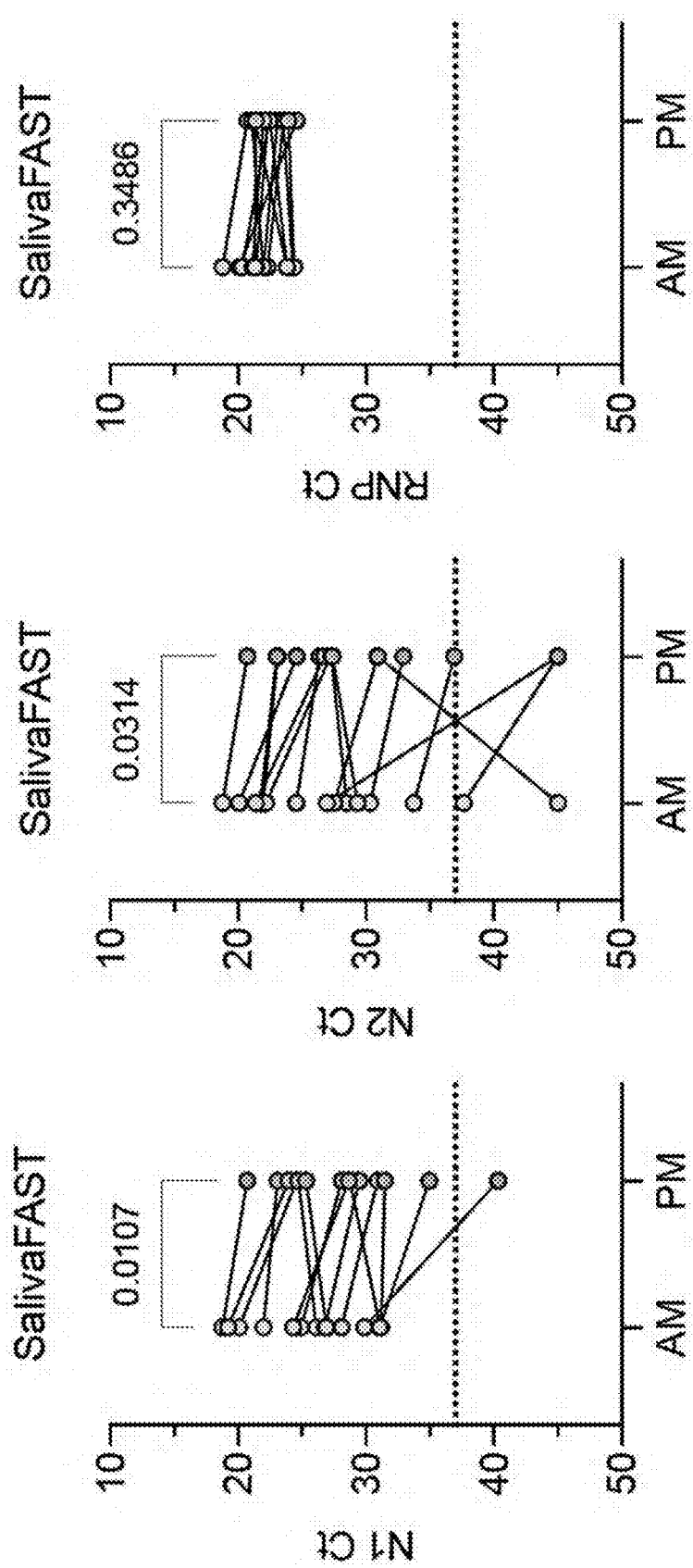
Figure 15:
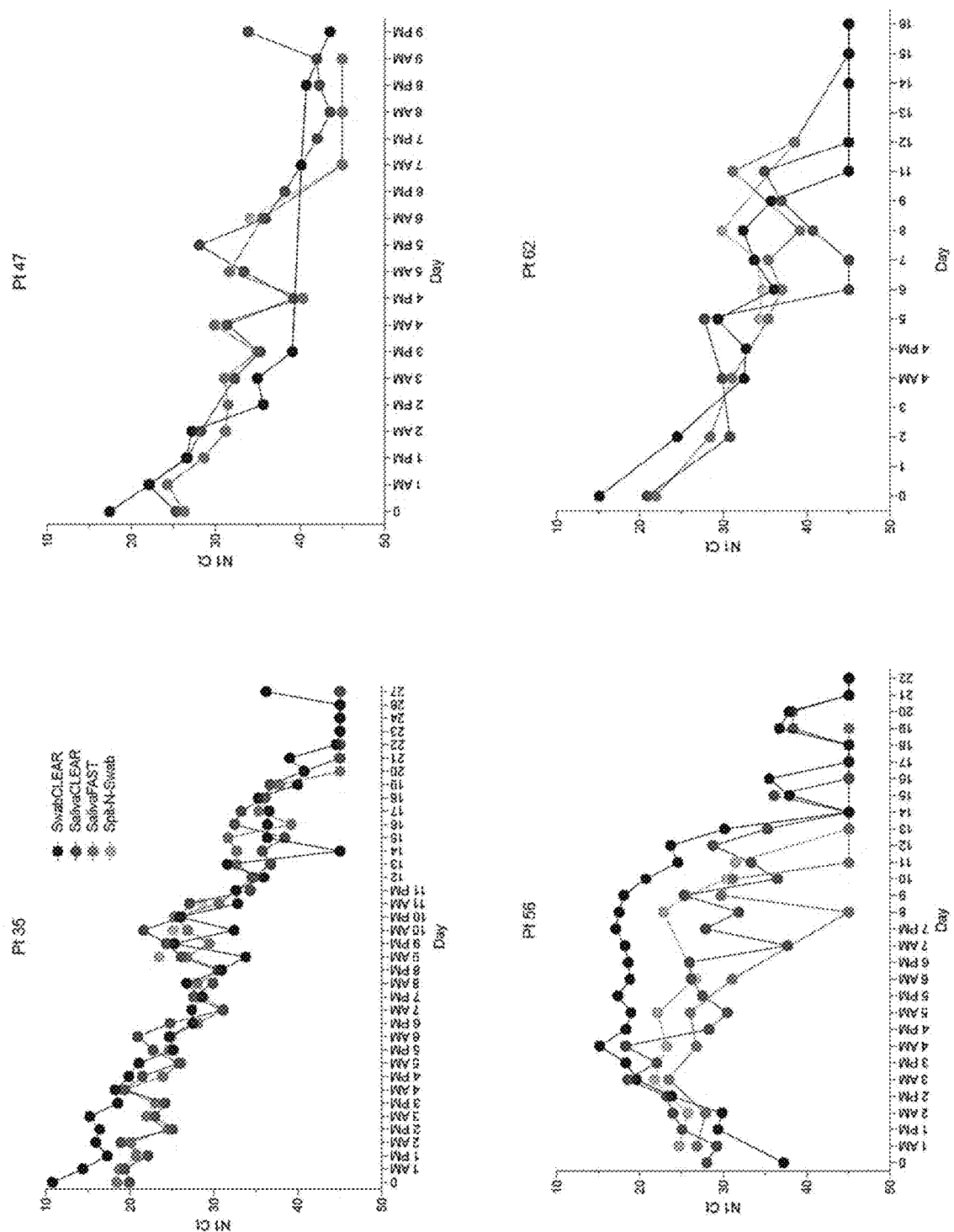
FIG. 15 shows graphs illustrating viral load monitoring in COVID-19 patients from diagnosis to viral clearance. The Ct values are presented for matched SwabCLEAR (blue), SalivaCLEAR (purple), SalivaFAST (magenta), and Spit-N-Swab (pink) specimens collected longitudinally over 5 to 21 days from COVID-19 patients.
Figure 15:
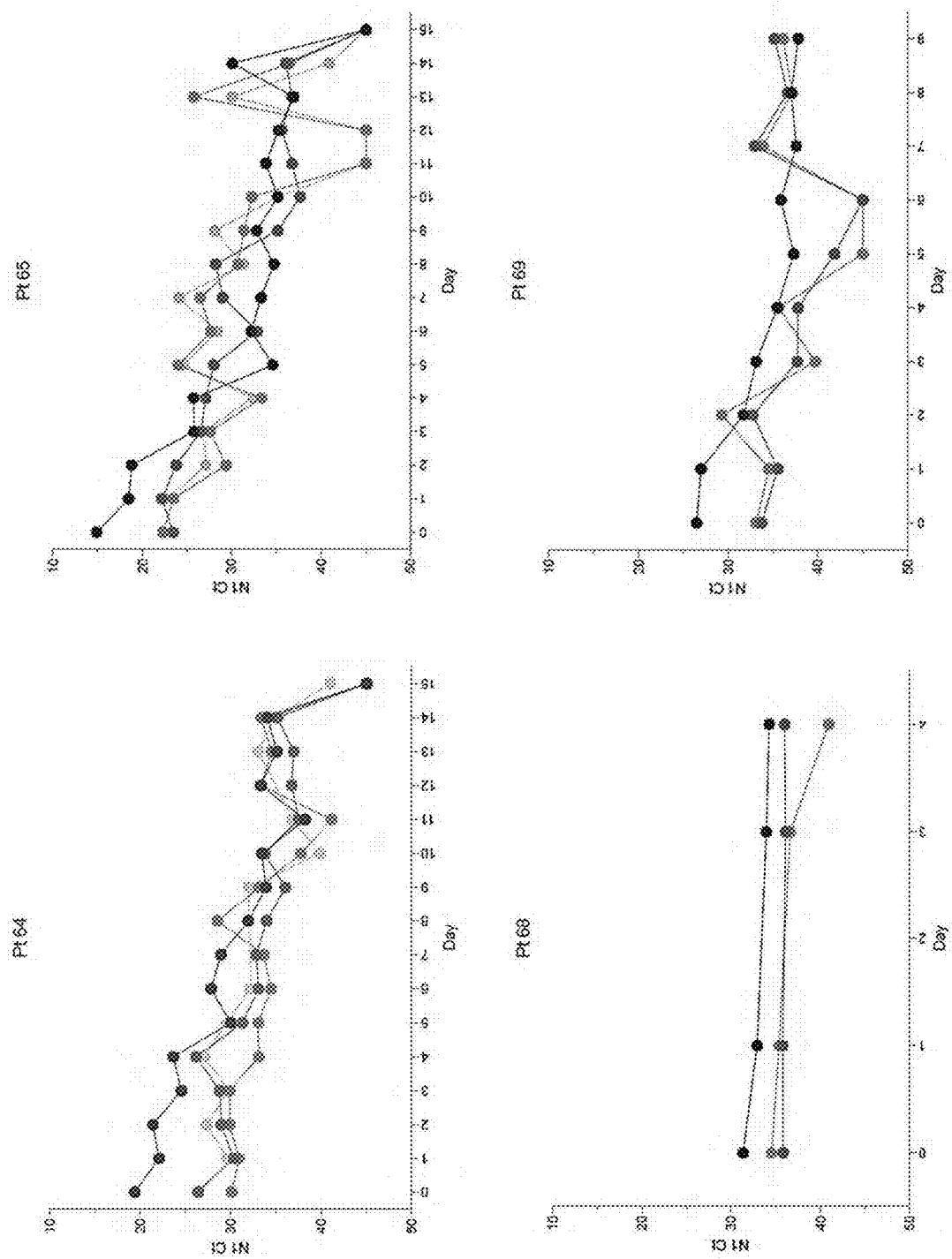
Figure 15:
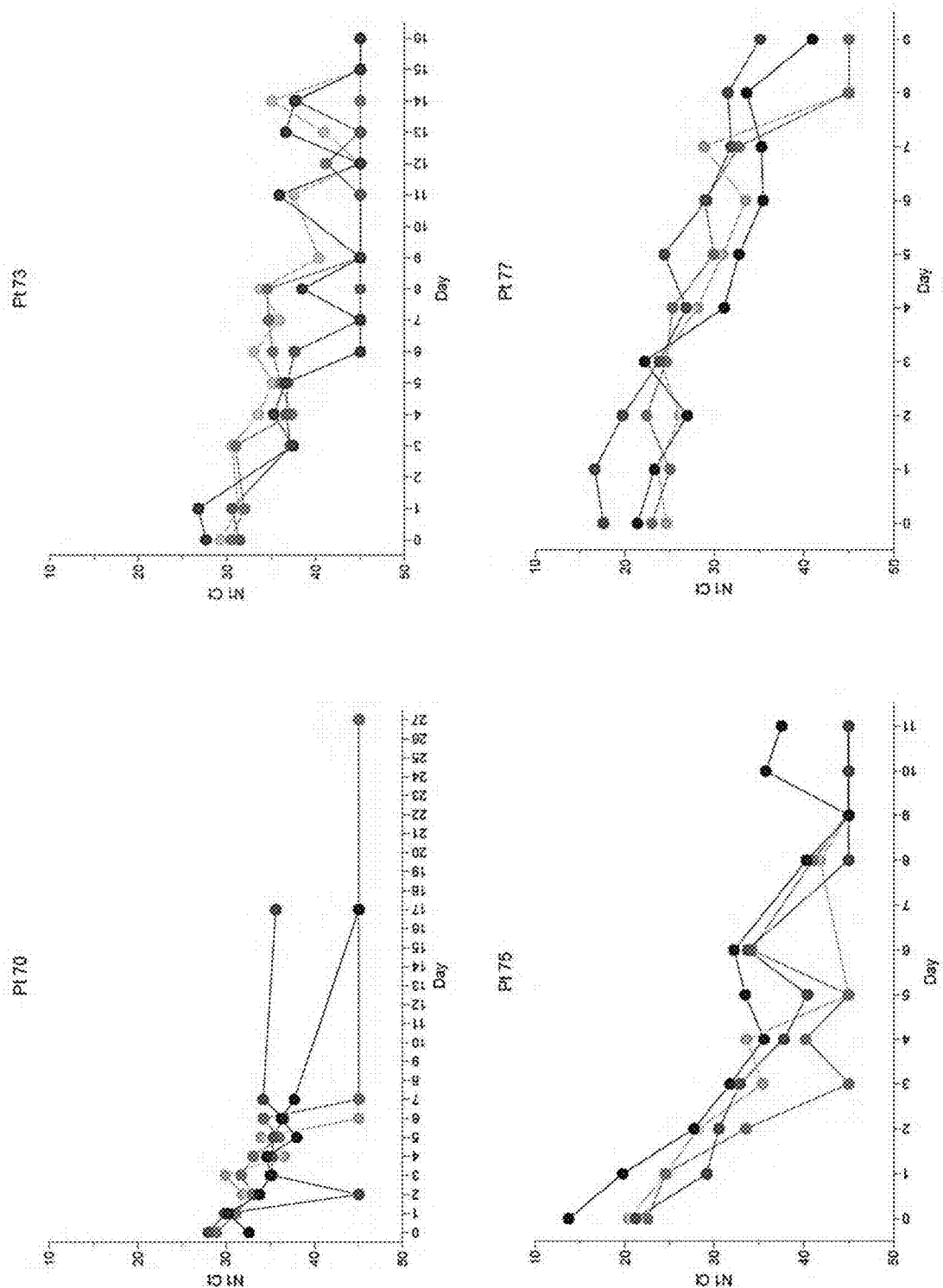
Figure 15:
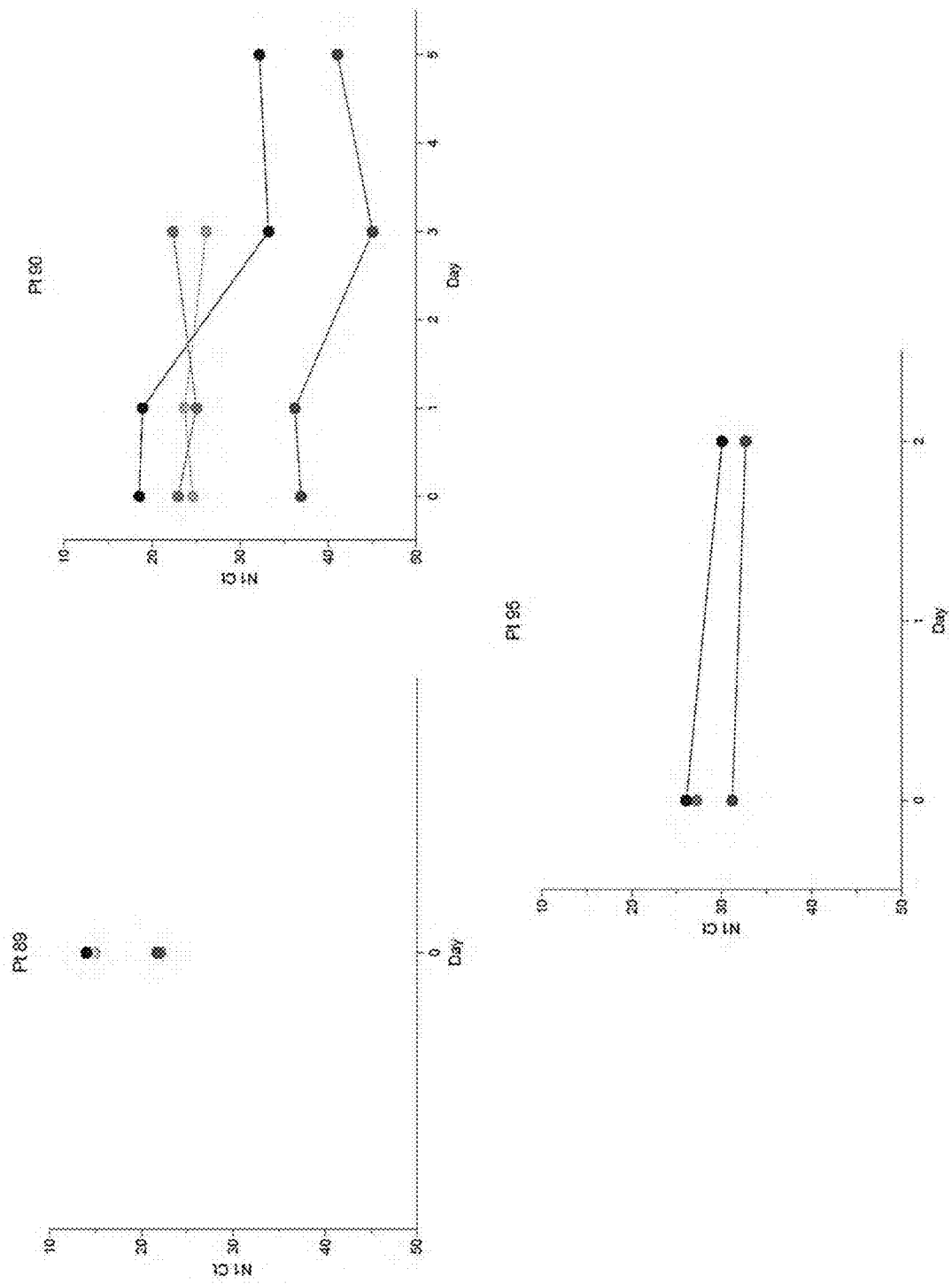

COVID-19 patients underwent longitudinal monitoring up to 27 days after symptom onset to observe the natural course of convalescence and viral clearance (see FIG. 15). Many matched sample sets were collected in the morning and afternoon on the same day. Comparison of the RNP Ct value in the morning versus the afternoon demonstrated a slight Ct value increase of 0.69 in SwabCLEAR and 1.1 in SalivaCLEAR (see FIGS. 14A and 14B), suggesting diurnal change in the sample matrix. However, this difference was not observed for SalivaFAST (see FIG. 14C). There was a trend for afternoon specimens to have decreased viral load compared to morning saliva specimens. This change was most pronounced for SalivaFAST, which demonstrated an Ct increase of 2.78 for N1 (p=0.011 and 2.58 for N2 (p=0.031) (see FIG. 14C). Overall, these preliminary data raise the possibility that diurnal variation in saliva matrix may could impact the clinical sensitivity of RT-qPCR.

Multiplex Assay for Simultaneous Detection of Influenza and SARS-CoV-2 Viruses

In another aspect, a method of detecting multiple analytes from the same sample is provided. In particular, in some embodiments, multiple viral infections can be detected from the same biological sample in accordance with extraction-free, direct-PCR techniques described herein. For example, methods of the present invention may be used to detect a coronavirus infection, such SARS-CoV-2 while also detecting another respiratory pathogen, such as influenza viruses.

More specifically, the present invention provides a multiplex assay (FLUVIDFast test), which is a real-time RT-qPCR multiplexed test intended for the simultaneous qualitative detection and differentiation of SARS-CoV-2, influenza A virus, and/or influenza B virus nucleic acid in upper or lower respiratory specimens (spit or swab samples) collected and processed via unique buffer compositions of the present invention.

Exemplary methods of performing the FLUVIDFast test include obtaining a biological sample from an individual. The biological sample may be any tissue or body fluid sample, most notably a saliva sample (e.g., collected via having patients spit into an appropriate collection vessel) or respiratory mucosa (e.g., collected via nasopharyngeal or throat swabs). Such sample collection may be in a similar manner as that described with reference to Example 1, previously described herein.

Furthermore, similar to the methods previously described herein (with regard to the COVIDFast testing methods), the multiplex assay avoids conventional approaches that require nucleic acid extraction steps and, instead, sample testing is direct and avoids the extraction process. In particular, the clinical samples are provided in a unique buffer composition, in which nucleic acid is directly used for downstream qPCR, rtPCR, or NGS-based diagnostic testing. The unique buffer composition is previously described herein.

The step of performing PCR assays for the FLUVIDFast test includes using viral nucleic acid specific primer-probe sets. In the present example, the viral nucleic acid specific primer-probe sets used in the FLUVIDFast test include the CDC Influenza SARS-CoV-2 (Flu SC2) Multiplex Assay Primers and Probes (published on CDC website at: https://www.cdc.gov/coronavirus/2019-ncov/lab/multiplex-primer-probes.html, last updated on Jul. 13, 2021). The FLUVIDFast test further includes quantifying viral nucleic acid, which may include performing at least one of quantitative PCR (qPCR) and digital PCR (dPCR), which may include droplet digital PCR (ddPCR). Based on the results, a patient can be diagnosed as either having been or not been infected with SARS-CoV-2, influenza A, and/or influenza B viruses.

Clinical Validation of FLUVIDFast Testing:

The FLUVIDFast assay was run on 450 residue clinical swab samples from daily COVID19 test.

The FLUVIDFast tests were clinically validated against COVIDFast tests for SARS-CoV-2 detection. 450 paired clinical samples—i.e., each testing subject provided one saliva sample and one anterior nares swab sample—from community members were analyzed by FLUVIDFast and compared to COVIDFast. The PPA and the NPA are 92.86% and 99.24%, respectively (see Table 3 below).

TABLE 3

Clinical validation of FLUVIDFast against COVIDFast

| COVIDFast | | FLUVIDFast | | |
|---|---|---|---|---|
| | | +(pos) | −(neg) | |
| | +(pos) | 52 | 4 | 56 |
| | −(neg) | 3 | 391 | 394 |
| | | 55 | 395 | 450 |

PPA—92.86% (52/56)
NPA = 99.24% (391/394)

The results of the FLUVIDFast test, specifically the ability to detect influenza A and influenza B, are provided in Table 4 below:

TABLE 4

| FLUVIDFast Detection of Influenza A, B, and SARS-CoV-2 | | | |
|---|---|---|---|
| | FAM - FluA | VIC - FluB | 610-SARS-CoV-2 |
| Positive | 8 | 0 | 55 |
| Negative | 442 | 450 | 395 |
| TOTAL | 450 | 450 | 450 |
| Percentage | 1.77% | 0% | 12.22% |

Figure 17:
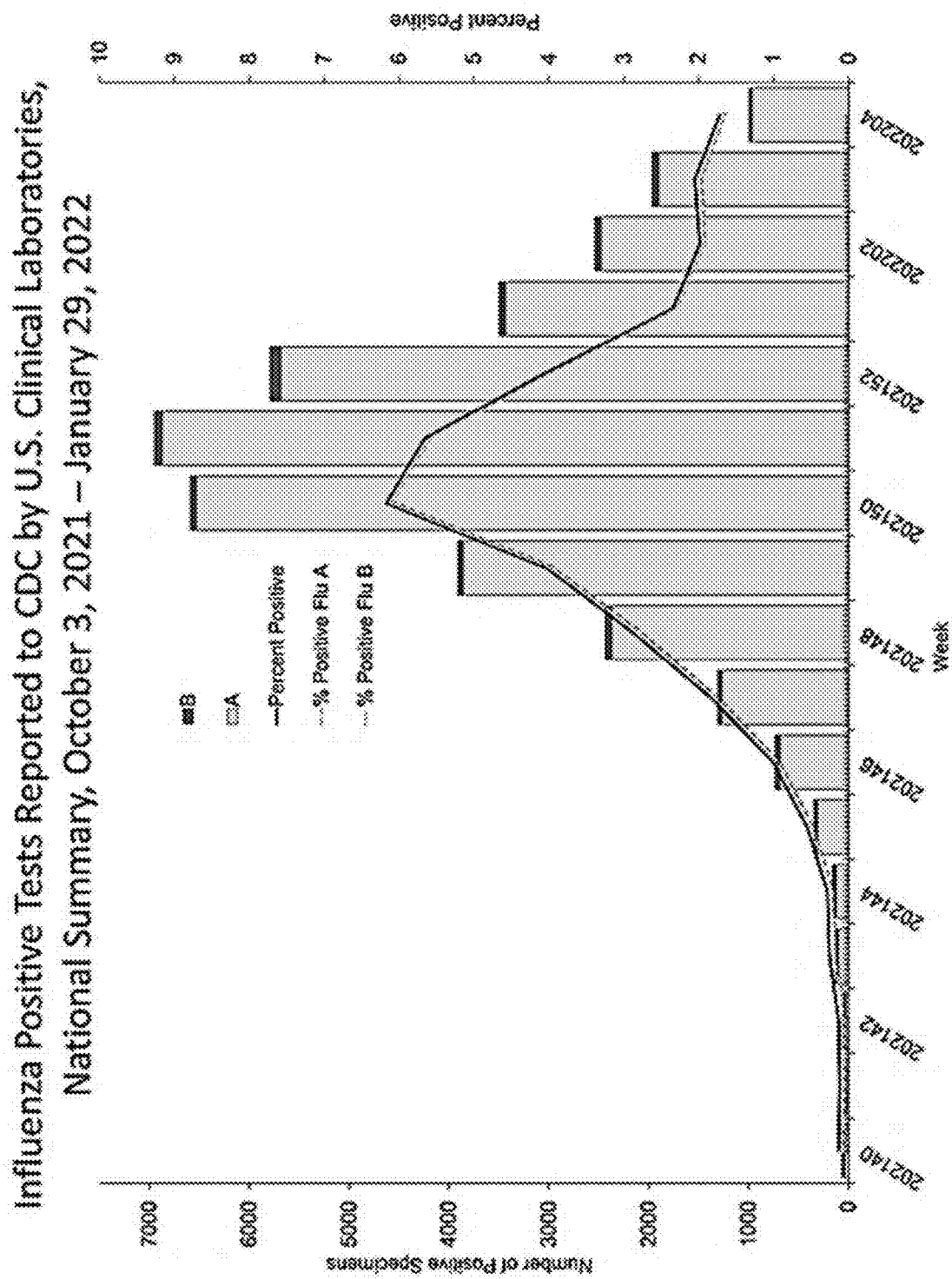
FIG. 17 is a graph showing influenza positive tests reported to the Centers for Disease Control (CDC) by U.S. clinical laboratories.

FLUVIDFast (4-plex assay) was run on 450 residue clinical swab samples from daily COVID19 test. As shown in the table (Table 4), influenza A was detected and influenza B was not detected. All 8 cases of influenza were influenza A only, with no co-infection with COVID19. One possible reason for no detection of influenza B is suggested by a recent influenza positive test reported to the CDC (see FIG. 16). In particular, the incidence of influenza B is very low, at 2.3%, in comparison with 97.7% of influenza A. Accordingly, regardless of the type of test used, finding positive influenza B clinical samples could be a challenge. The incidence of influenza A in the FLUVIDFast test similar to that in the most recent summary as reported to the CDC by U.S. clinical laboratories (see week 202204 in FIG. 17).

Figure 18A:
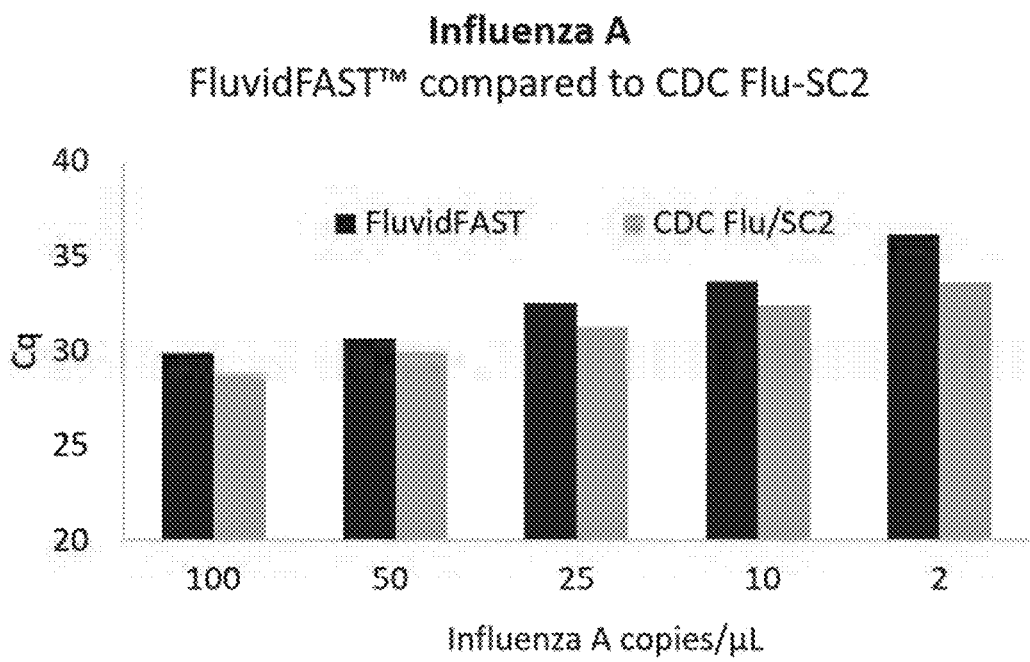
FIGS. 18A and 18B are graphs comparing the effectiveness of detecting influenza A and influenza B via the extraction-free method of a FLUVIDFast assay versus the CDC Influenza SARS-CoV-2 (Flu SC2) Multiplex Assay, which requires RNA extraction, in which Cq values at different concentrations of influenza A and influenza B copies are plotted for comparison.
Figure 18B:
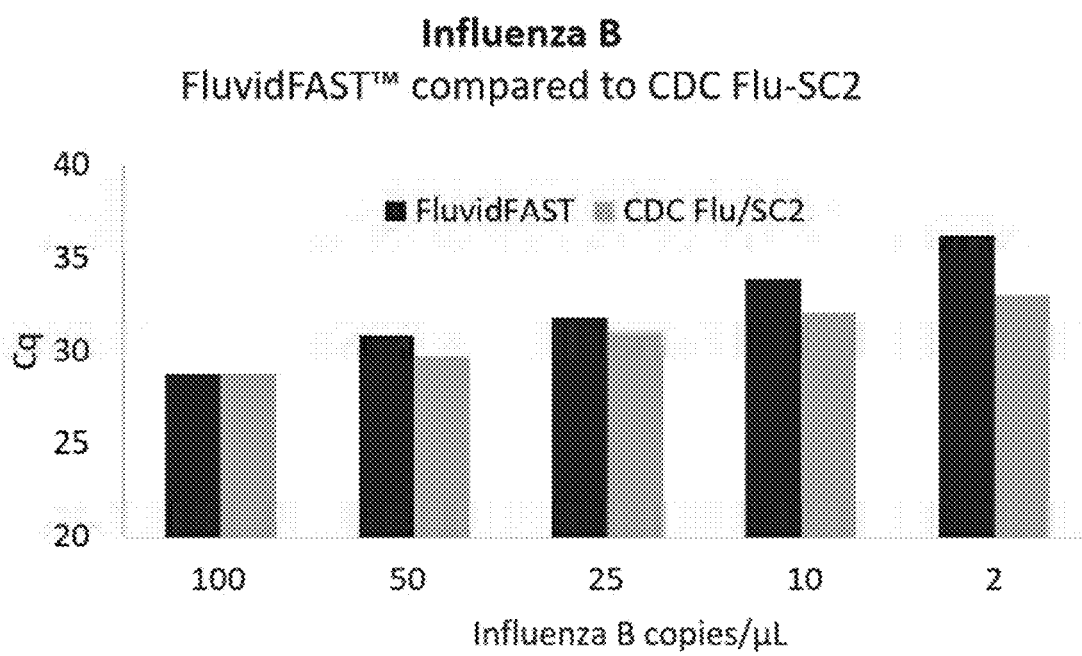

The inventors found that FLUVIDFast test was more effective at detecting influenza A and influenze B strains than the CDC's current Flu-SC2 multiplex assay. In particular, FIGS. 18A and 18B are graphs comparing the effectiveness of detecting influenza A and influenza B, respectively, via the extraction-free method of a FLUVIDFast assay versus the CDC Influenza SARS-CoV-2 (Flu SC2) Multiplex Assay, which requires RNA extraction. In FIGS. 18A and 18B, Cq values at different concentrations of influenza A and influenza B copies are plotted for comparison.

FIG. 19 is a chart showing a Limit of Detection (LoD) determination using twenty replicates of influenza A and influenza B and 10 replicates of SARS-CoV-2 contrived samples at concentrations ranging from 3 to 10 copies/µL.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for extraction-free analysis of nucleic acid, the method comprising the steps of:
    mixing a saliva sample comprising nucleic acids with a buffer comprising nuclease-free water, an antifungal, an antibiotic, a ribonuclease inhibitor, and a reducing agent;
    inactivating, with proteinase K, a virus in the sample;
    amplifying, without performing a nucleic acid extraction, a target viral nucleic acid to form amplicons within the sample; and
    analyzing the amplicons to detect presence of the target viral nucleic acid.

2. The method of claim 1, wherein said target viral nucleic acid is RNA or DNA.

3. The method of claim 1, wherein said analyzing step comprises sequencing the amplicons.

4. The method of claim 1, wherein the reducing agent is Tris (2-carboxyethyl) phosphine.

5. The method of claim 1, wherein the antifungal comprises Amphotericin B and the antibiotic comprises Penicillin and/or Streptomycin.

6. The method of claim 1, further comprising a step of obtaining the sample via a nasal or throat swab.

7. The method of claim 1, wherein the target viral nucleic acid is from severe acute respiratory syndrome coronavirus-2 (SARS-COV-2).

8. The method of claim 7, wherein the amplifying step uses primers specific to one or more of the N, ORF1ab, and E genes of severe acute respiratory syndrome coronavirus-2 (SARS-COV-2).

9. The method of claim 1, further comprising a step of quantifying the target viral nucleic acid.

10. The method of claim 9, wherein the amplifying step comprises quantitative PCR (qPCR).

11. The method of claim 9, further comprising a step of comparing target viral nucleic acid quantities in a plurality of samples at successive time points and determining disease progression based on increases or decreases in the target viral nucleic acid quantities over time.

12. The method of claim 11, further comprising a step of predicting disease outcomes based on the viral nucleic acid quantity.

13. A method for extraction-free analysis of nucleic acid, the method comprising the steps of:
    mixing a saliva sample comprising said nucleic acids with a buffer comprising nuclease-free water, an antifungal, an antibiotic, a ribonuclease inhibitor, and a reducing agent;
    inactivating, with heat, a virus in the sample;
    amplifying, without performing a nucleic acid extraction, a target viral nucleic acid to form amplicons within the sample; and
    analyzing the amplicons to detect presence of the target viral nucleic acid.

14. The method of claim 1, wherein the reducing agent breaks bonds in a protein in the sample.

15. The method of claim 14, wherein the reducing agent improves efficacy of the Proteinase K.

16. The method of claim 15, wherein the reducing agent is Tris (2-carboxyethyl) phosphine.

17. The method of claim 13, wherein the step of inactivating comprises heating the sample and buffer at 95° C. for 5 minutes.

* * * * *